(12) United States Patent
Dodge et al.

(10) Patent No.: US 6,444,688 B1
(45) Date of Patent: Sep. 3, 2002

(54) COMPOUNDS AND COMPOSITIONS WITH NITROGEN-CONTAINING NON-BASIC SIDE CHAINS

(75) Inventors: Jeffrey A. Dodge; Charles D. Jones, both of Indianapolis, IN (US); Kristin Marron, San Diego, CA (US); James P. Sluka, Greenwood; Mark G. Stocksdale, South Bend, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/476,288

(22) Filed: Jun. 7, 1995

(51) Int. Cl.[7] .................. A61K 31/445; A61K 31/38; C07D 333/56; C07D 409/12

(52) U.S. Cl. ............... 514/324; 514/277; 514/319; 514/320; 514/337; 514/422; 514/428; 546/196; 546/202; 546/205; 546/269; 546/274; 546/340; 546/342; 548/525; 548/527; 548/575; 548/576

(58) Field of Search .................. 546/196, 202, 546/205, 269, 274, 340, 342; 548/525, 527, 575, 576; 514/277, 319, 320, 324, 337, 422, 428

(56) References Cited

U.S. PATENT DOCUMENTS

| | | | | |
|---|---|---|---|---|
| 3,947,470 A | * | 3/1976 | Brenner | 549/57 |
| 3,975,537 A | * | 8/1976 | Hill et al. | 514/469 |
| 4,133,814 A | | 1/1979 | Jones et al. | 546/202 |
| 4,358,593 A | | 11/1982 | Jones et al. | 546/202 |
| 4,380,635 A | | 4/1983 | Peters | 546/202 |
| 4,418,068 A | | 11/1983 | Jones | 514/320 |
| 4,851,554 A | * | 7/1989 | Kennedy et al. | 549/471 |
| 5,395,842 A | * | 3/1995 | Labrie et al. | 514/320 |
| 5,446,061 A | * | 8/1995 | Bryant et al. | 514/456 |
| 5,482,958 A | * | 1/1996 | Bryant et al. | 514/408 |
| 5,523,309 A | * | 6/1996 | Bryant | 514/320 |
| 5,567,828 A | * | 10/1996 | Dodge | 549/51 |
| 5,631,247 A | * | 5/1997 | Dodge | 514/177 |

FOREIGN PATENT DOCUMENTS

| | | |
|---|---|---|
| EP | 062503 A1 | 10/1982 |
| EP | 584852 A1 | 3/1994 |
| EP | 617030 A1 | 9/1994 |
| WO | 02893 * | 4/1989 |
| WO | 89/02893 * | 4/1989 |
| WO | WO95/10513 | 4/1995 |

OTHER PUBLICATIONS

Jones et al., "Antiestrogens. 2. Structure–Activity studies in a series of 3–aroyl–2arylbenzo[b]thiophene . . . " J. Med. Chem. v.28, 1057–1066, 1984.*

Burger "A guide to the chemical basis of drug design" p. 15, 1983.*

Fuchs–Young, et al., "Inhibition of Estrogen–Stimulated Growth of Uterine Leiomyomas by Selective Estrogen Receptor Modulators", Molecular Carcinogenesis, 17:151–159 (1996).

* cited by examiner

*Primary Examiner*—Ceila Chang
(74) *Attorney, Agent, or Firm*—Gary M. Birch; Gilbert T. Voy

(57) ABSTRACT

The instant invention provides compounds of formula I

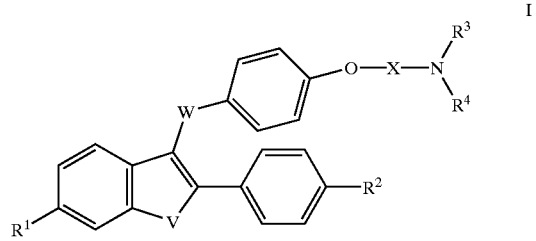

wherein $R^1$ is OH, O—C(O)—($C_1$–$C_6$ alkyl), O—C(O)—O ($C_1$–$C_6$ alkyl), O—C(O)—Ar, or O—C(O)—O—Ar;

$R^2$ is H, OH, O($C_1$–$C_6$ alkyl), O—C(O)—($C_1$–$C_6$ alkyl), O—C(O)—O($C_1$–$C_6$ alkyl), O—C(O)—Ar, O—C(O)—O—Ar, O—$SO_2$—($C_4$–$C_6$ alkyl), chloro, fluoro, or bromo;

V is S, O, or $CH_2CH_2$;

W is CHOH, C(O), or $CH_2$;

X is $(CH_2)_n$;

$R^3$ and $R^4$ each, independently, are H, $C_1$–$C_6$ alkyl, C(O)—($C_1$–$C_6$ alkyl), C(O)—NH—($C_1$–$C_6$ alkyl), C(O)—Ar, or together with the nitrogen to which they are attached form a 5- or 6-membered imide or cyclic amide;

n is 1, 2, or 3; and

Ar is optionally substituted phenyl;

povided that at least one of $R^3$ and $R^4$ contains a carbonyl functional group, and their use in the treatment of estrogen deficiency pathologies.

20 Claims, No Drawings

COMPOUNDS AND COMPOSITIONS WITH NITROGEN-CONTAINING NON-BASIC SIDE CHAINS

FIELD OF THE INVENTION

This invention relates to the fields of pharmaceutical and organic chemistry and provides novel compounds with nitrogen-containing non-basic side chains, which are useful for the treatment of the various medical indications associated with post-menopausal syndrome, and uterine fibroid disease, endometriosis, and aortal smooth muscle cell proliferation. The present invention also relates to pharmaceutical compositions of the compounds of the present invention.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern: osteoporosis, cardiovascular effects such as hyperlipidemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body.

One of the most common types of osteoporosis is that associated with menopause. Most women lose from about 20% to about 60% of the bone mass in the trabecular compartment of the bone within 3 to 6 years after the cessation of mensus. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the bio-mechanical strength of the overall structure.

In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hall-marks of post-menopausal osteoporosis.

At this time, the only generally accepted method for treatment of post-menopausal osteoporosis is estrogen replacement therapy. Although therapy is generally successful, patient compliance with the therapy is low primarily because estrogen treatment frequently produces undesirable side effects.

Prior to menopause, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women undergoing estrogen replacement therapy experience a return of serum lipid concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, Tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new compounds, pharmaceutical compositions thereof, and methods of using such compounds for the treatment of post-menopausal syndrome and other estrogen-related pathological conditions such as those mentioned below. The reduction of bone density and mass leading to osteoporosis that more rarely occurs in men is also tied to the loss of hormonal regulation and is, therefore, also a target for therapy according to the compounds and methods of the current invention.

Uterine fibrosis is an old and ever present clinical problem known by a variety of names, including uterine hypertrophy, uterine lieomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formation of abdominal adhesions and infections. In some patients, initial surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis.

Endometriosis is a condition of severe dysmenorrhea, which is accompanied by severe pain, bleeding into the endometrial masses or peritoneal cavity and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen; however, it is sometimes necessary to use continuous estrogen to control the symptoms. This use of estrogen can often lead to undersirable side effects and even the risk of endometrial cancer.

Another treatment consists of continuous administration of progestins which induces amenorrhea and by suppressing ovarian estrogen production can cause regressions of the endometrial growths. The use of chronic progestin therapy is often accompanied by the unpleasant CNS side effects of progestins and often leads to infertility due to suppression of ovarian function.

A third treatment consists of the administration of weak androgens, which are effective in controlling the endometriosis; however, they induce severe masculinizing effects. Several of these treatments for endometriosis have also been implicated in causing a mild degree of bone loss with continued therapy. Therefore, new methods of treating endometriosis are desirable.

Aortal smooth muscle cell proliferation plays an important role in diseases such as atherosclerosis and restenosis. Vascular restenosis after percutaneous transluminal coronary angioplasty (PTCA) has been shown to be a tissue response characterized by an early and late phase. The early phase occuring hours to days after PTCA is due to thrombosis with some vasospasms while the late phase appears to be dominated by excessive proliferation and migration of aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology* 8: 369–375 (Aug. 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'", Hermans et al., *American Heart Journal* 122: 171–187 (July 1991).

In the pathogenesis of restenosis, excessive cell proliferation and migration occurs as a result of growth factors produced by cellular constituents in the blood and the damaged arterial vessel wall, which factors mediate the proliferation of smooth muscle cells in vascular restenosis.

Agents that inhibit the proliferation and/or migration of aortal smooth muscle cells are useful in the treatment and prevention of restenosis. The present invention provides for the use of compounds as aortal smooth muscle cell proliferation inhibitors and, thus, inhibitors of restenosis.

SUMMARY OF THE INVENTION

The present invention provides compounds with nitrogen-containing non-basic side chains of formula I

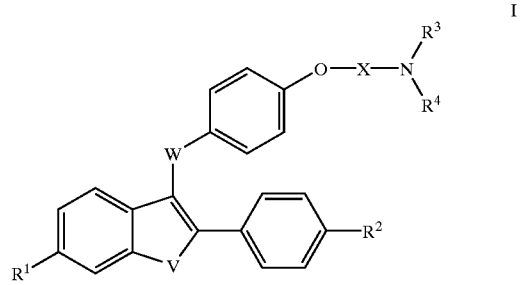

wherein $R^1$ and $R^2$, independently, are H, OH, O($C_1$-$C_6$ alkyl), O—C(O)—($C_1$-$C_6$ alkyl), O—C(O)—O($C_1$-$C_6$ alkyl), O—C(O)—Ar, O—C(O)—O—Ar, O—$SO_2$—($C_4$-$C_6$ alkyl), chloro, fluoro, or bromo;

V is S, O, or $CH_2CH_2$;

W is CHOH, C(O), or $CH_2$;

X is $(CH_2)_n$, or $(CH_2)_mC(O)$;

$R^3$ and $R^4$ each, independently, are H, $C_1$-$C_6$ alkyl, C(O)—($C_1$-$C_6$ alkyl), C(O)—NH—($C_1$-$C_6$ alkyl), C(O)—Ar, or together with the nitrogen to which they are attached form 1-pyrrolidinyl, 1-piperidinyl, or a 5- or 6-membered imide or cyclic amide;

m is 1 or 2;

n is 1, 2, or 3; and

Ar is optionally substituted phenyl;

provided that at least one of X, $R^3$, and $R^4$ contain a carbonyl functional group.

The present invention also provides compounds with nitrogen-containing non-basic side chains of formula II

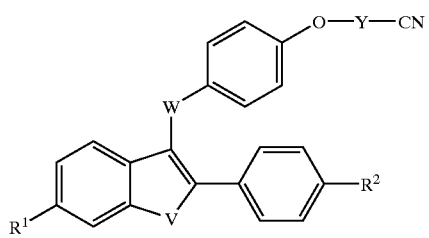

wherein $R^1$ and $R^2$, independently, are H, OH, O($C_1$–$C_6$ alkyl), O—C(O)—($C_1$–$C_6$ alkyl), O—C(O)—O($C_1$–$C_6$ alkyl), O—C(O)—Ar, O—C(O)—O—Ar, O—$SO_2$—($C_4$–$C_6$ alkyl), chloro, fluoro, or bromo;

V is S, O, or $CH_2CH_2$;

W is CHOH, C(O), or $CH_2$;

Y is $(CH_2)_n$, CH($C_1$–C4 alkyl);

n is 1, 2, or 3; and

Ar is optionally substituted phenyl.

The present invention further provides compounds with nitrogen-containing non-basic side chains of formula III

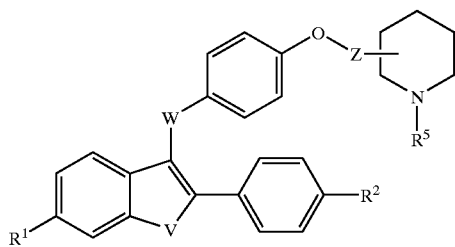

wherein $R^1$ and $R^2$, independently, are H, OH, O($C_1$–$C_6$ alkyl), O—C(O)—($C_1$–$C_6$ alkyl), O—C(O)—O($C_1$–$C_6$ alkyl), O—C(O)—Ar, O—C(O)—O—Ar, O—$SO_2$—($C_4$–$C_6$ alkyl), chloro, fluoro, or bromo;

V is S, O, or $CH_2CH_2$;

W is CHOH, C(O), or $CH_2$;

Z is a bond or $CH_2$;

$R^5$ is C(O)—($C_1$–$C_6$ alkyl); and

Ar is optionally substituted phenyl.

Compounds of the current invention may have an asymmetric center. Thus, such compounds can have an R- or S-configuration, or a mixture thereof. All such isomers are considered part of this invention.

The present invention also provides pharmaceutical compositions containing compounds of formula I, formula II, and formula III, optionally containing estrogen or progestin, and the use of such compounds, alone or in combination with estrogen or progestin, for alleviating the symptoms of post-menopausal symptoms, particularly osteoporosis, cardiovascular related pathological conditions, and estrogen-dependent cancer. As used herein, the term "estrogen" includes steroidal compounds having estrogenic activity such as, for example, 17β-estradiol, estrone, conjugated estrogen (e.g., Premarin®), equine estrogen, 17α-ethynyl estradiol, and the like. As used herein, the term "progestin" includes compounds having progestational activity such as, for example, progesterone, norethynodrel, norgestrel, megestrol acetate, norethindrone, and the like.

The present invention further provides the use of the compounds of the present invention for inhibiting uterine fibroid disease and endometriosis in women and aortal smooth muscle cell proliferation, particularly restenosis, in humans.

DETAILED DESCRIPTION OF THE INVENTION

General terms used in the description of compounds of the present invention bear their usual meanings. For example, "$C_1$–$C_4$ alkyl" refers to aliphatic chains of 1 to 4 carbon atoms including methyl, ethyl, propyl, isopropyl, butyl, n-butyl, and the like; and "$C_1$–$C_6$ alkyl" encompasses the groups included in the definition of "$C_1$–$C_4$ alkyl" in addition to groups such as pentyl, isopentyl, hexyl, isohexyl, and the like. "$C_4$–$C_6$ alkyl" refers to aliphatic chains of 4 to 6 carbon atoms including butyl, n-butyl, pentyl, isopentyl, hexyl, isohexyl, and the like.

The term "substituted phenyl" refers to a phenyl group having one or more substituents selected from the group consisting of $C_1$–$C_4$ alkyl, $C_1$–$C_5$ alkoxy, hydroxy, nitro, chloro, fluoro, or tri(chloro or fluoro)methyl. "$C_1$–$C_5$ alkoxy" represents a $C_1$–$C_5$ alkyl group attached through an oxygen bridge such as, for example, methoxy, ethoxy, n-propoxy, isopropoxy, and the like.

It should also be understood that as used herein, references to alkyl and alkoxy structures also include cycloalkyl and cycloalkoxy groups where the number of carbons within the structure is at least 3.

Further, "imide" is understood to indicate a heterocyclic structure wherein a nitrogen atom is adjacent to two carbonyl functional groups. An "amide" is understood to be a structure having a nitrogen atom adjacent to a single carbonyl functional group, such amide may be cyclic.

Preferred compounds of this invention include compounds of formula I wherein any or all of the following limitations apply: V is S; W is C(O); and X is $(CH_2)_2$ or $CH_2C(O)$, especially $(CH_2)_2$. Especially preferred compounds of formula I are those wherein all of the preceding limitations apply.

Other preferred compounds of formula I include those compounds wherein $R^1$ and $R^2$ are OH, O—C(O)—($C_1$–$C_6$ alkyl), O—C(O)—O($C_1$–$C_6$ alkyl), O—C(O)—Ar, or O—C(O)—O—Ar, especially OH or $OCH_3$. Of these, compounds wherein $R^1$ and $R^2$ are the same as one another are particularly preferred.

Certain $R^3$ and $R^4$ groups also demonstrate preferable characteristics. For example, those compounds of formula I wherein $R^3$ and $R^4$ together with the nitrogen to which they are attached form 1-pyrrolidinyl, 1-piperidinyl, or a 5- or 6-membered imide or cyclic amide are preferred. A further preferred subgroup of the preferred 1-pyrrolidinyl, 1-piperidinyl, imide, and cyclic amide compounds include those compounds wherein $R^1$ and $R^2$ are OH or $OCH_3$.

Most especially preferred compounds of formula I include those having all of the aforementioned limitations, that is, compounds wherein V is S; W is C(O); X is $(CH_2)_2$ or $CH_2C(O)$, especially $(CH_2)_2$; $R^1$ and $R^2$ are OH, O—C(O)—($C_1$–$C_6$ alkyl), O—C(O)—O($C_1$–$C_6$ alkyl), O—C(O)—Ar, and O—C(O)—O—Ar, especially OH or $OCH_3$, particularly wherein $R^1$ and $R^2$ are the same as one another; and $R^3$ and $R^4$, together with the nitrogen to which they are attached form 1-pyrrolidinyl, 1-piperidinyl, or a 5- or 6-membered imide or cyclic amide.

In keeping with the scope of this invention, the preferred compounds of formula I are limited to those wherein at least one carbonyl functional group is present at a position adjacent to the nitrogen in the 3- side chain. That is, at least one of X, $R^3$, and $R^4$ must contain a carbonyl functional group.

Other preferred compounds of this invention include compounds of formula II wherein any or all of the following limitations apply: V is S; W is C(O); and Y is $CH_2$ or $CH(CH_3)$. Especially preferred compounds of formula II are those wherein all of the preceding limitations apply.

Other preferred compounds of formula II include those compounds wherein $R^1$ and $R^2$ are OH, O—C(O)—($C_1$–$C_6$ alkyl), O—C(O)—O($C_1$–$C_6$ alkyl), O—C(O)—Ar, or O—C(O)—O—Ar, especially OH or $OCH_3$. Of these, compounds wherein $R^1$ and $R^2$ are the same as one another are particularly preferred.

Yet other preferred compounds of this invention include compounds of formula III wherein any or all of the following limitations apply: V is S; W is C(O); and Z is a bond or $CH_2$. Especially preferred compounds of formula III are those wherein all of the preceding limitations apply.

Other preferred compounds of formula II include those compounds wherein $R^1$ and $R^2$ are OH, O—C(O)—($C_1$–$C_6$ alkyl), O—C(O)—O($C_1$–$C_6$ alkyl), O—C(O)—Ar, or O—C(O)—O—Ar, especially OH or $OCH_3$. Of these, compounds wherein $R^1$ and $R^2$ are the same as one another are particularly preferred.

Preferred methods of this invention obviously include those wherein preferred compounds are used.

The compounds of the present invention are derivatives of benzo[b]thiophene which is named and numbered according to the Ring Index, The American Chemical Society, as follows.

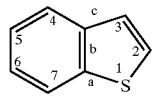

In the processes for preparing the compounds of the present invention, the starting material is generally a precursor of formula below, which can be prepared via known

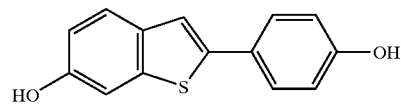

Typically, the two hydroxy groups are protected by known hydroxy protecting groups that are capable of resisting acylation under standard Friedel-Crafts conditions and subsequent reduction by a strong reducing agent. Preferred hydroxy protecting groups are $C_1$–$C_4$ alkyl, and methyl is especially preferred. See, e.g., U.S. Pat. Nos. 4,133,814; 4,380,635; and 4,418,068, each of which is herein incorporated by reference, J. W. Barton, "Protective Groups in Organic Chemistry", J. G. W. McOmie (ed.), Plenum Press, New York, N.Y., 1973, Chapter 2, and T. W. Green, "Protective Groups in Organic Synthesis", John Wiley and Sons, New York, N.Y., 1981, Chapter 7.

Following preparation of the desired protected precursor, the precursor is acylated, using standard Friedel-Crafts conditions, according to acylation methods disclosed in the above-incorporated United States patents.

All reagents obtained from commercial sources were used without further purification unless otherwise indicated. $^1$H-NMR and $^{13}$C-NMR were measured as indicated at 300 and 75 MHz respectively. $^1$H-NMR chemical shifts are reported as δ values in ppm relative to the NMR solvent employed. $^1$H-NMR coupling constants are reported in Hertz (Hz) and refer to apparent multiplicities. Multiplicity is indicated as follows: s (singlet), d (doublet), t (triplet), q (quartet), m (multiplet), comp (complex), br (broad), and app (apparent). Column chromatography was performed according to the method of Still et. al. (Still, W. C.; Kahn, M.; Mitra, A. J. Org. Chem. 1978, 43:2923) unless otherwise indicated with EM Science silica gel (230–400 mesh ASTM). Radial chromatography was performed on a Chromatotron (Harrison Research) using 1, 2, or 4 mm thick plates. All air and/or moisture sensitive reactions were run under an argon or nitrogen atmosphere in rigorously dried glassware. In all cases, concentrations were performed under reduced pressure with a rotary evaporator.

Four general synthetic routes, which were used to prepare compounds of the present invention, are outlined below, wherein $R^1$ and $R^2$ are as defined above.

General Route #1:

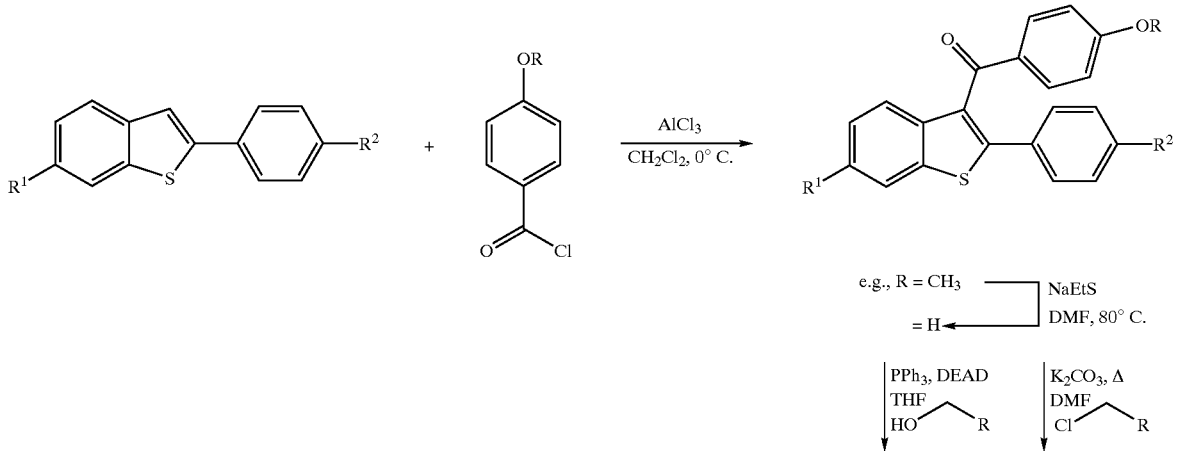

-continued
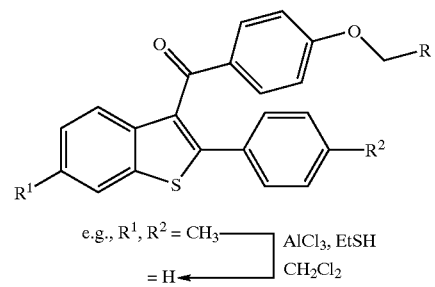
General Route #2:
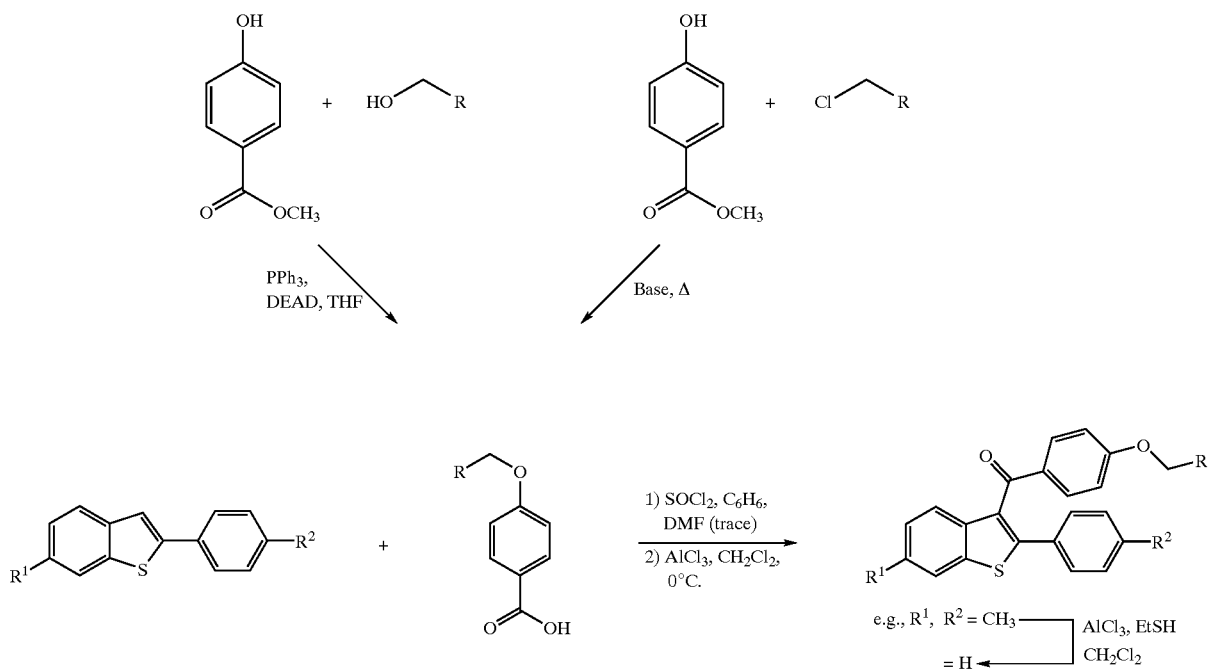
General Route #3:
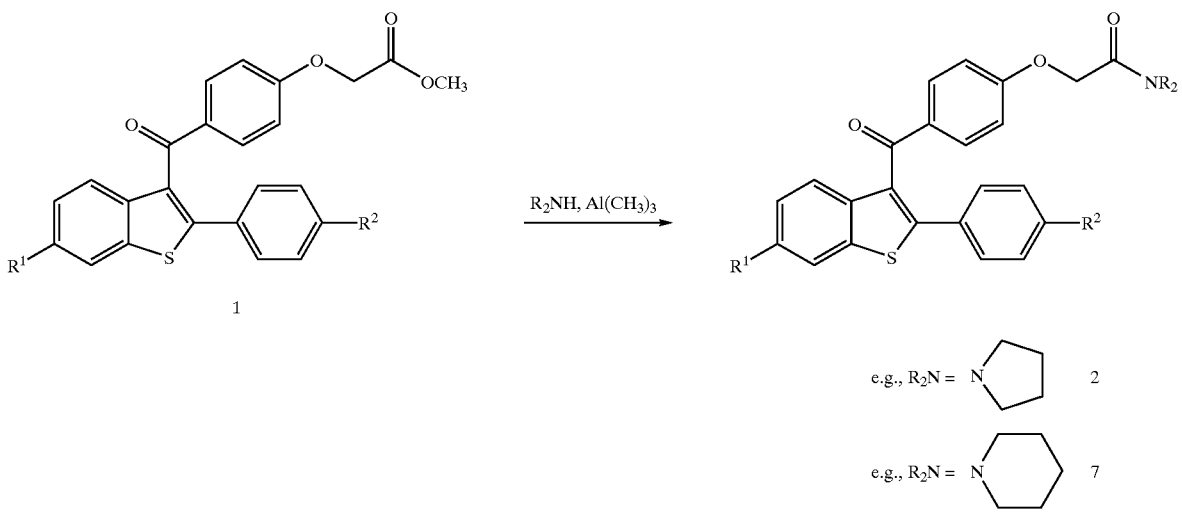
General Route #4:

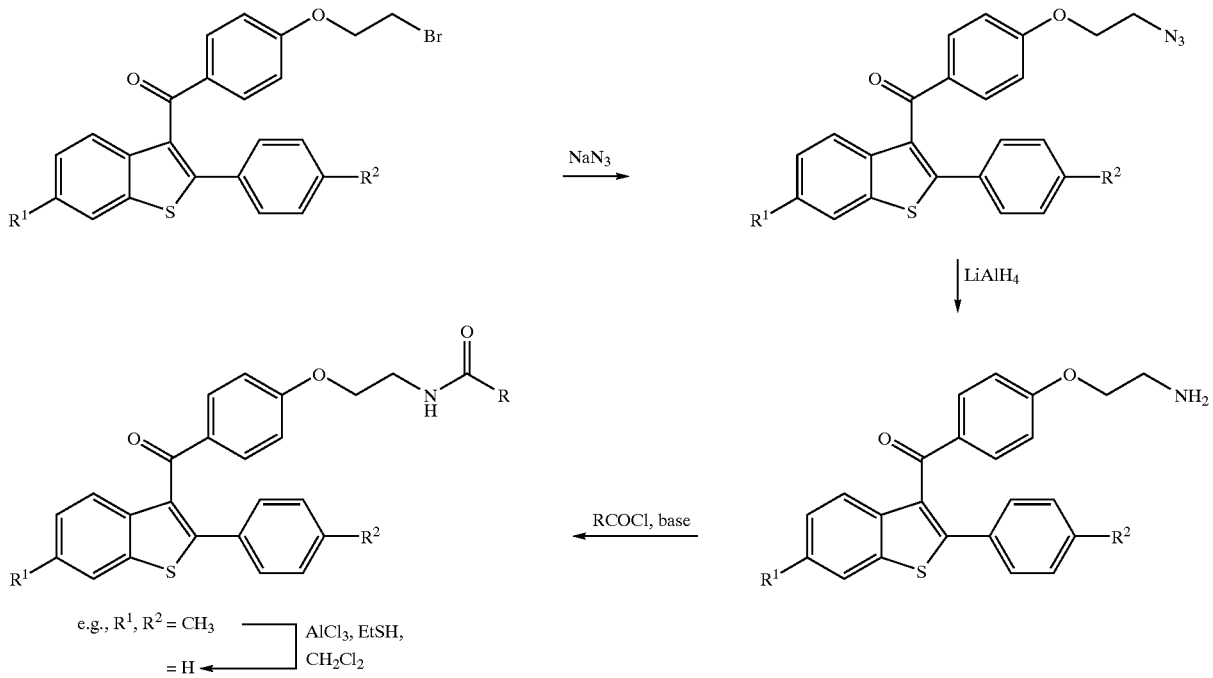

Compounds of the present invention in which W is CHOH are prepared following sodium ethanethioate deprotection by dissolution in an appropriate solvent and reaction with reducing agent, such as, for example, lithium aluminum hydride, under an inert gas such as nitrogen.

The amount of reducing agent used in this reaction is an amount sufficient to reduce the carbonyl group to an alcoholic group (CHOH). Generally, an excess of the reducing agent per equivalent of the substrate is used.

Suitable solvents include any solvent or mixture of solvents that will remain inert under reducing conditions, such as, for example, diethyl ether, dioxane, and tetrahydrofuran (THF). The anydrous form of these solvents is preferred, and anhydrous THF is especially preferred.

The temperature employed in this step is that which is sufficient to effect completion of the reduction reaction. Ambient temperature, in the range from about 17° C. to about 25° C., generally is adequate.

The length of time for this step is that amount necessary for the reaction to occur. Typically, this reaction takes from about 1 to about 20 hours. The optimal time can be determined by monitoring the progress of the reaction via conventional chromatographic techniques.

A compound of the present invention wherein W is CHOH may be further reduced to provide compounds wherein W is methylene via standard procedures. This is accomplished by suspending the compound in an appropriate solvent and cooling under an inert gas such as nitrogen. To this suspension is added a suitable trialkyl silane reducing agent, preferably triethyl silyl, and a reasonably strong protic acid such as hydrochloric acid, trifluoroacetic acid, and the like.

Suitable solvents can be any solvent or mixture of solvents that remain inert under the reaction conditions employed in the process. For example, halogenated alkane solvents such as dichloromethane and 1,2-dichloroethane, as well as haloaromatics such as chlorobenzene and the like may be used. of these, dichloromethane is preferred.

The temperature employed in this step is that which is sufficient to effect completion of the present reduction process. Typically, the reaction is cooled to about 0° C. and the reaction solution is kept on ice until the reaction is complete; however, ambient temperature also is satisfactory. In general, this reaction is completed in less than three hours, and the progress of the reaction can be monitored via standard techniques. The product of this reaction is extracted and purified via standard techniques.

Alternatively, ketones of the type shown in general route #1 prior to alkylation can be reduced to the compound wherein W is methylene. In this process, the $R^1$ and $R^2$ hydroxy protecting groups, which are preferrably methyl, optionally are removed, and the protected or deprotected compound is reacted with a reducing agent such as lithium aluminum hydride in the presence of an inert solvent having a boiling point in the range from about 150° C. to about 200° C. While each step of this process is preferably carried out in separate vessels, it is possible to carry out each step of the present process in the same vessel.

The amount of reducing agent used in this reaction is an amount sufficient to reduce the carbonyl group to a methylene group. Generally, an excess of the reducing agent per equivalent of the substrate is used.

The solvent used in the present process is required to have a relatively high boiling point, in the range from about 150° C. to about 200° C., as represented by solvents such as, for example, n-propylbenzene, diglyme (1,1'-oxybis[2-methoxyethane]), and anisole, and Red-Al® (sodium bis(2-methoxyethoxyaluminum hydride)), which also is used as the reducing agent. When the $R^1$ and $R^2$ substituents of compounds of the present invention are hydroxy protecting groups, n-propylbenzene is the preferred solvent. When such protecting groups are first optionally removed prior to reduction, Red-Al is the preferred reagent.

The temperature used in this reaction is that which is sufficient to complete the reduction reaction. Preferably, the reaction mixture is heated to reflux for about 15 minutes to about 6 hours, and allowed to cool to ambient temperature. When $R^1$ and $R^2$ are hydroxy protecting groups, a small amount of deionized water is added to the mixture followed by the addition of a small aliquot of 15% sodium hydroxide.

When $R^1$ and $R^2$ are OH, the reaction is carefully quenched with excess 1.0 N hydrochloric acid. The optimal amount of time for these reactions to run, typically from about 10 minutes to about 3 hours, can be determined by monitoring the progress of the reaction via standard techniques.

Following reduction of W to CHOH or $CH_2$, the appropriate groups can be appended on as described previously.

When a $O-C(O)-(C_1-C_6$ alkyl) or $O-C(O)-Ar$ group is desired at $R^1$ and $R^2$, a dihydroxy compound of formula I, II, or III is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger, such as a tertiary amine, has been added. If desired, acylation catalysts such as 4-dimethylaminopyridine or 4-pyrollidinopyridine may be used. See, e.g., Haslam, et al., *Tetrahedron*, 36:2409–2433 (1980).

The acylation reactions which provide the aforementioned $R^1$ and $R^2$ groups are carried out at moderate temperatures in the range from about −25° C. to about 100° C., frequently under an inert atmosphere such as nitrogen gas. However, ambient temperature is usually adequate for the reaction to run.

Such acylations of the hydroxy group also may be performed by acid-catalyzed reactions of the appropriate carboxylic acids in inert organic solvents or heat. Acid catalysts such as sulfuric acid, polyphosphoric acid, methanesulfonic acid, and the like are used.

The aforementioned $R^1$ and $R^2$ groups also may be provided by forming an active ester of the appropriate acid, such as the esters formed by such known reagents as dicyclohexylcarbodiimide, acylimidazoles, nitrophenols, pentachlorophenol, N-hydroxysuccinimide, and 1-hydroxybenzotriazole. See, e.g., *Bull. Chem. Soc. Japan*, 38:1979 (1965), and *Chem. Ber.*, 788 and 2024 (1970).

Each of the above techniques that provide $O-C(O)-(C_1-C_6$ alkyl) and $O-C(O)-Ar$ groups are carried out in solvents as discussed above. These techniques, which do not produce an acid product in the course of the reaction, of course, do not necessitate the use of an acid scavenger in the reaction mixture.

When a compound is desired in which $R^1$ and $R^2$ is $O-SO_2-(C_4-C_6$ alkyl), a dihydroxy compound is reacted with, for example, a derivative of the appropriate sulfonic acid such as a sulfonyl chloride, bromide, or sulfonyl ammonium salt, as taught by King and Monoir, *J. Am. Chem. Soc.*, 97:2566–2567 (1975). The dihydroxy compound also can be reacted with the appropriate sulfonic anhydride. Such reactions are carried out under conditions such as were explained above in the discussion of reaction with acid halides and the like.

Compounds of formula I, II, and III can be prepared so that $R^1$ and $R^2$ are different biological protecting groups or, preferably, the same biological protecting group. Preferred protecting groups include $OCH_3$, $O-C(O)-C(CH_3)_3$, $O-C(O)-C_6H_5$, and $O-SO_2-(CH_2)_3-CH_3$.

The term "biological protecting groups" refers to those $R^1$ and $R^2$ substituents which delay, resist, or prohibit removal of such groups in a biological system such as, for example, following administration of a compound of the present invention containing the above-described $R^1$ and $R^2$ groups to a human. Such compounds also are useful for the methods herein described, especially when W is $CH_2$.

The following preparations and examples are presented to further illustrate the preparation and use of compounds of the present invention. It is not intended that the invention be limited in scope by reason of any of the following preparations and examples. The compound numbers correspond to those given in Table 1.

PREPARATION 1

Preparation of compound 1:

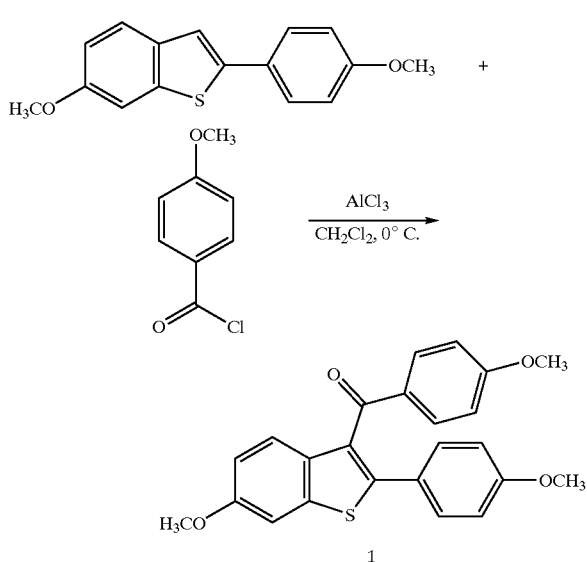

p-Anisoyl chloride (1.54 g, 9.00 mmol, Aldrich Chemical Company) was dissolved in anhydrous $CH_2Cl_2$ (100 ml). To this stirred solution was added 6-methoxyphenyl-2-(4-methoxyphenyl)-benzo[b]thiophene (1.62 g, 6.00 mmol) prepared by the method of Jones et al. (*J. Med. Chem.* 1984, 27:1057). The resulting mixture was cooled to 0° C., and $AlCl_3$ (1.20 g, 9.00 mmol) was added in small portions over a five minute period. After one hour the reaction mixture was poured into ice water (150 ml) and extracted with $CH_2Cl_2$ (3×75 ml). The organic layers were combined and washed with 1N NaOH (30 ml), water (25 ml), and brine (25 ml). The organic layers were then dried over $MgSO_4$. After removal of the solvent, the resulting crude product was flash chromatographed on a silica gel column (eluent: ethyl acetate:hexanes; 3:7) giving 2.253 g (93%) of a light yellow solid. The product was further purified by recrystallization from acetone/methanol to yield 2.109 g (87%) of compound 1.

IR (CHCl$_3$) $v_{max}$ 3020, 3015, 2970, 2940, 2840, 1600, 1475, 1253, 1218, 1167; $^1$H-NMR (300 MHz, DMSO d$_6$) δ 7.64–7.69 (m,3H), 7.29–7.32 (m, 3H). 6.86–7.00 (m, 5H), 3.83 (s, 3H) 3.76 (s, 3H). $^{13}$C-NMR (75.489 MHz, DMSO d$_6$) δ 192, 163.61, 159.47, 157.35, 141, 139.36, 133.17, 131.81, 130, 129.63, 125.17, 123.26, 115.00, 114.35, 114.07, 105.11, 55.49, 55.13; FD$^+$-MS for $C_{24}H_{20}O_4S$=404. Elemental Analysis $C_{24}H_{20}O_4S$- Calculated: C, 71.27; H, 4.98; S, 7.93; O, 15.82; Found: C, 71.50; H, 5.00; S, 7.98; O, 15.77.

PREPARATION 2

Preparation of compound 2:

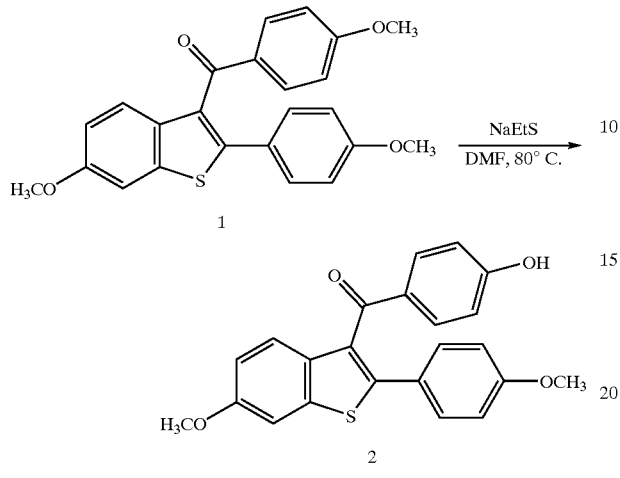

Compound 1 (0.405 g, 1.00 mmol) was dissolved in 2 ml of dry DMF. To this stirred solution was added 3.0 ml of 0.50 M sodium ethanethioate (NaEtS) in DMF. The reaction temperature was increased to 80° C. for four hours. The reaction was diluted with ethyl acetate (10 ml), and water was added (10 ml). The mixture was then neutralized with 1N HCl and extracted with ethyl acetate (3×20 ml). The organic extracts were combined, washed with brine (4×20 ml), dried over $MgSO_4$, and evaporated under reduced pressure to give a pale yellow solid. The solid was further purified by radial chromatography (2 mm plate, eluting solvent 5% ethyl acetate/$CH_2Cl_2$). Yield of compound 2 as a foamy yellow solid was 0.307 g (79%).

IR (CHCl$_3$) $v_{max}$ 3585, 3265, 3022, 3012, 2970, 2940, 2840, 1602, 1476, 1254, 1163; $^1$H-NMR (CDCl$_3$) δ 7.70–7.73 (d,2H,J=8.6 Hz), 7.52–7.55 (d, 1H, J=8.5 Hz), 7.31–7.34 (m, 3H), 6.94–6.98 (dd, 1H, J=9.0 Hz, J=2.4 Hz), 6.73–6.76 (d, 2H, J=8.7 Hz), 6.66–6.69 (d, 2H, J=9.1 Hz), 3.88 (s, 3H), 3.74 (s, 3H); $^{13}$C-NMR (CDCl$_3$) δ 192.92, 159.95, 158.58, 156.47, 141.91, 138.89, 132.71, 131.67, 129.16, 129.09, 128.85, 124.72, 122.82, 114.27, 113.70, 112.95, 103.39, 54.49, 54.08; FD+-MS for $C_{23}H_{18}O_4S$=390. Elemental Analysis $C_{23}H_{18}O_4S$ -Calculated: C, 70.75; H, 4.65; Found: C, 70.93; H, 4.56.

EXAMPLE 1

Preparation of compound 25:

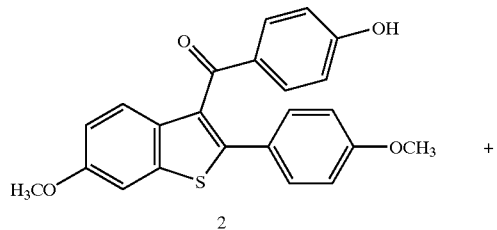

Compound 2 (1.23 g, 3.17 mmol) and 1-trimethylacetyl piperidine-2-methanol (1.58 g, 7.91 mmol) were dissolved in anhydrous THF (50 ml). To this stirred solution was added PPh$_3$ (1.66 g, 6.33 mmol) followed by diethylazodicarboxylate (DEAD) (1.00 ml, 6.33 mmol) via syringe, and the reaction mixture was stirred at room temperature for 18 hours. The solvent was removed under reduced pressure, and the resulting mixture was rotary chromatographed (dichloromethane eluent) to yield 1.64 g (91%) of compound 25 as product.

IR (CHCl$_3$) $v_{max}$ 3008, 2943, 1615, 1601, 1476, 1254, 1165; $^1$H-NMR (CDCl$_3$) δ 7.74–7.77 (d, 2H, J=9 Hz), 7.48–7.51 (d, 1H, J=9 Hz), 7.31–7.35 (m, 3H), 6.93–6.96 (dd, 1H, J=9 Hz, J=2 Hz), 6.74–6.80 (m, 4H), 3.88 (s, 3H), 3.75 (s, 3H), 1.3–4.4 (m, 20H); $^{13}$C-NMR (CDCl$_3$) δ 193.26, 177.26, 162.87, 159.75, 157.65, 142.42, 140.07, 133.99, 132.36, 130.58, 130.25, 126.01, 124.03, 114.79, 114.24, 114.09, 104.51, 65.84, 61.75, 55.63, 55.25, 38.94, 28.46, 27.19, 25.49, 25.04, 19.35; FD$^+$-MS for $C_{34}H_{37}O_5S$=571.

EXAMPLE 2

Preparation of compound 22:

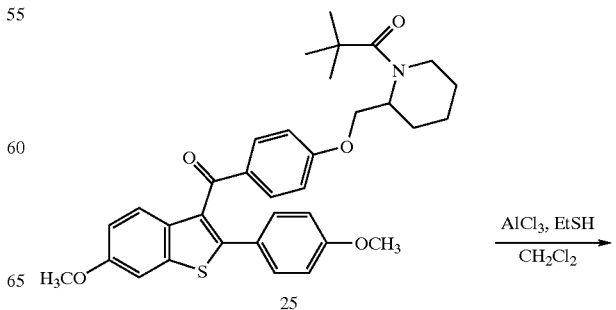

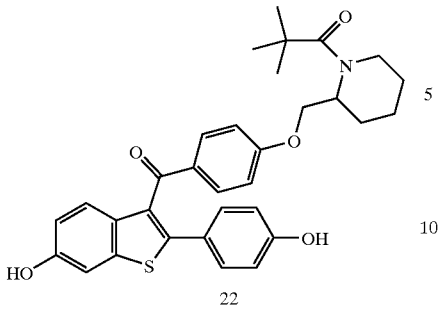

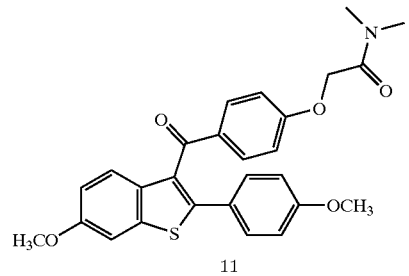

Compound 25 (1.24 g, 2.17 mmol) was dissolved in CH$_2$Cl$_2$ (50 ml). To this stirred solution was added ethanethiol (EtSH) (0.80 ml, 10.8 mmol) and AlCl$_3$ (1.73 g, 13.0 mmol). This reaction mixture was stirred vigorously for 30 minutes, and then quenched with brine and saturated NaHCO$_3$. Any residue was dissolved by the addition of methanol and ethyl acetate. The pH was adjusted to just basic. The mixture was then diluted with ethyl acetate (200 ml). After separation of the aqueous layer, the organic layer was washed with potassium sodium tartrate (3×75 ml) and then brine (2×75 ml). The organic ethyl acetate layer was dried over MgSO$_4$ and evaporated under reduced pressure. The product was isolated by rotary chromatography (4 mm plate, eluting solvent 5:4:1 ethyl acetate:hexanes:triethylamine) yielding 0.929 g of compound 22 as a yellow solid (79%).

IR (CHCl3) $v_{max}$ 3298, 3025, 3010, 2946, 1600, 1262, 1166; $^1$H-NMR (MeOD d$_4$) δ 7.68–7.71 (d, 2H, J=8.8 Hz), 7.38–7.41 (d, 1H, J=8.7 Hz), 7.24–7.25 (d, 1H, J=2.5 Hz), 7.16–7.19 (d, 2H, J=8.6 Hz), 6.83–6.87 (m, 3H), 6.60–6.63 (d, 2H, J=8.6 Hz), 1.35–4.20 (m, 11H), 1.25 (s, 9H); $^{13}$C-NMR (MeOD d$_4$) δ 194.39, 178.33, 163.40, 158.07, 155.62, 142.72, 140.28, 133.19, 132.37, 130.62, 130.24, 130.09, 124.89, 123.62, 115.38, 114.93, 114.28, 106.82, 65.17, 50.36, 38.89, 27.70, 25.53, 25.16, 19.09; FD$^+$-MS for C$_{32}$H$_{33}$O$_5$ S=543; Elemental Analysis C$_{32}$H$_{33}$O$_5$S -Calculated: C, 70.69; H, 6.12; N, 2.58; Found: C, 70.47; H, 6.13; N, 2.34.

EXAMPLE 3

Preparation of compound 11:

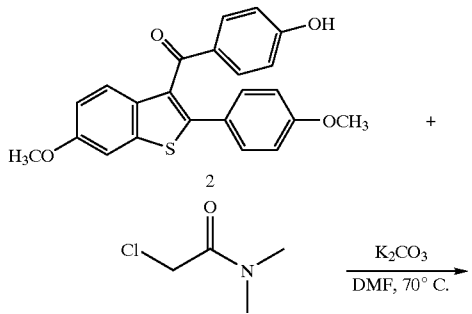

Compound 2 (3.0 g, 7.69 mmol) was dissolved in DMF (100 ml) and heated to 70° C. To this stirred solution was added K$_2$CO$_3$ (10.6 g, 76.8 mmol) followed by N,N-Dimethyl chloroacetamide (3.74 g, 30.8 mmol). The reaction mixture was heated to 100° C. and allowed to stir for 24 hours. The solvent was removed under reduced pressure, and the resulting mixture was dissolved in MeOH and salts were filtered. The crude reaction mixture was recrystallized in H$_2$O/methanol (2:1) to yield 2.81 g (77%) of compound 11 as product.

$^1$H-NMR (CDCl$_3$) δ 7.90 (d, 2H, J=9.7 Hz), 7.65 (d, 1H, J=9.7 Hz), 7.45 (d, 2H, J=9.7 Hz), 7.43 (s, 1H), 7.08 (dd, 1H, J=9.7 Hz), 6.93 (d, 2H, J=9.7 Hz), 6.87 (d, 2H, J=9.7 Hz), 4.78 (s, 2H), 4.00 (s, 3H), 3.87(s, 3H), 3.16(s, 3H), 3.08(s, 3H); FD$^+$-MS=475; Elemental Analysis C$_{27}$H$_{25}$NO$_5$S -Calculated: C, 68.19; H, 5.30; N, 2.94; Found: C, 68.46; H, 5.18; N, 2.99.

PREPARATION 3

Preparation of compound 27:

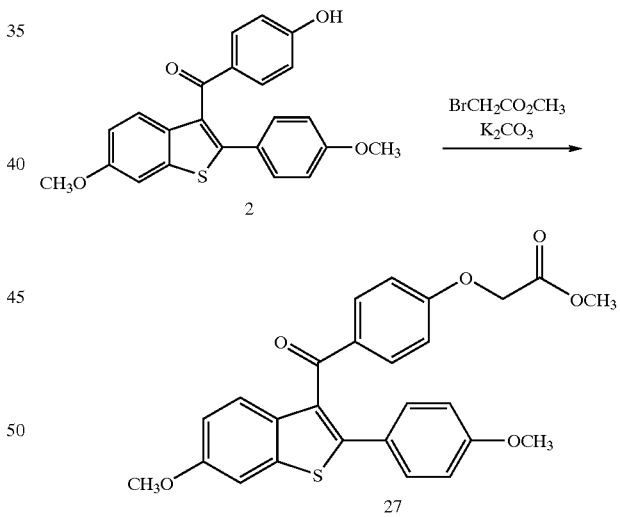

To a solution of phenol, compound 2 (5.0 g, 12.8 mmol) stirring in DMF at room temperature was added K$_2$CO$_3$ (5.3 g, 38.4 mmol) followed by methyl bromoacetate (8 ml, 84.5 mmol). The solution was heated to 80° C. for 1 h then cooled to room temperature and poured into brine/ethyl acetate (300 ml, 1:1). The mixture was extracted with ethyl acetate (3×100 ml) and the combined organic extracts washed thoroughly with brine, dried (MgSO$_4$) and filtered. Concentration gave a yellow syrup which was further dried under reduced pressure to yield 5.33 g (90%) of 27 as a white crystalline solid which was used without further purification.

$^1$H-NMR (CDCl$_3$) δ 7.78 (d, J=8.9 Hz, 2H), 7.51 (d, J=8.5 Hz, 1H), 7.30–7.35 (m, 3H), 6.96 (dd, J=9.0,2.3 Hz, 1H), 6.72–6.78 (overlapping d, 4H), 4.62 (s, 2H), 3.90 (s, 3H), 3.80 (s, 3H), 3.74 (s, 3H).

EXAMPLE 4

Preparation of compound 7:

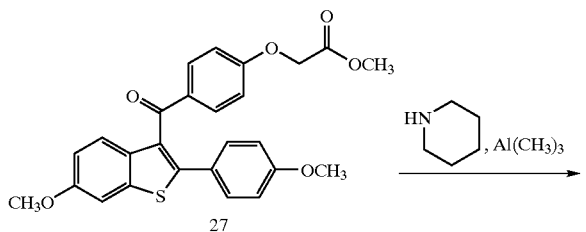

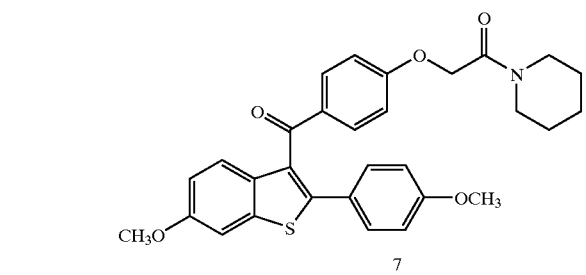

Reaction of compound 27 (0.42 g, 0.91 mmol), piperidine-hydrochloride (0.56mg, 4.58 mmol), and Al(CH$_3$)$_3$ (2.29 ml, 4.58 mmol) yielded 0.42 g (90%) of compound 7 as a tan foam.

$^1$H-NMR (CDCl$_3$) δ 7.79 (d, J=9.0 Hz, 2H), 7.52 (d, J=8.8 Hz, 1H), 7.30–7.35 (m, 3H), 6.96 (dd, J=9.0 Hz, 2.9 Hz, 1H), 6.82 (d, J=8.7 Hz, 2H), 6.78 (d, J=8.9 Hz, 2H), 4.66 (s, 2H), 3.90 (s, 3H), 3.75 (s, 3H), 3.53 (t, J=4.2 Hz, 2H), 3.42 (t, J=4.2 Hz, 2H), 1.49–1.69 (series of m, 6H); IR (CHCl$_3$) 1639 cm$^{-1}$; FD$^+$-MS 515 (M$^+$).

PREPARATION 4

Preparation of compound 28:

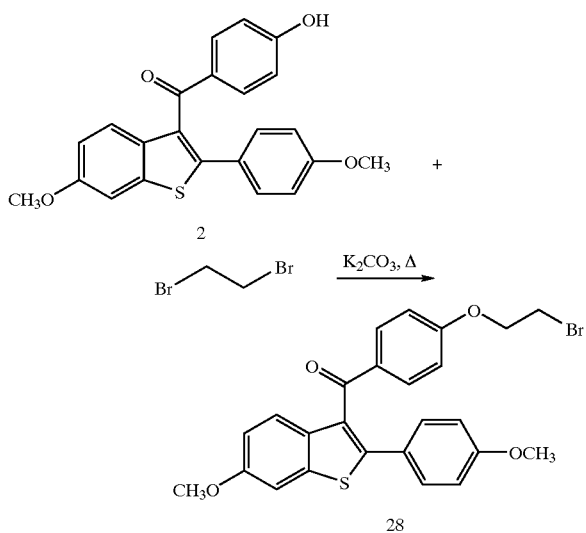

To compound 2 (3.90 g, 10.0 mmol), stirring in methyl ethyl ketone (25 ml), was added ground K$_2$CO$_3$ (2.07 g, 15.0 mmol) followed by 1,2-dibromoethane (10 ml). The solution brought to reflux and maintained at this temperature for 18 hr. The mixture was cooled to room temperature, filtered, and concentrated. Purification of the crude residue by flash column chromatography (8 cm×15 cm silica gel, 50% ethyl acetate in hexanes) gave compound 28 as a yellow solid 4.32 g (87%).

$^1$H-NMR (CDCl$_3$) δ 7.75–7.78 (d, 2H, J=8.8 Hz), 7.52–7.55 (d, 1H, J=8.9 Hz), 7.31–7.35 (m, 3H), 6.94–6.98 (dd, 1H, J=8.9 Hz, J=2.3 Hz), 6.74–6.78 (m, 4H); IR (CHCl$_3$) 3030, 3015, 2965, 2942, 2835, 1601, 1475,1253, 1240, 1167 cm$^{-1}$; FD$^+$-MS 496(Br79), 498 (Br81); Elemental Analysis C$_{25}$H$_{21}$BrO$_4$S -Calculated: C, 60.37; H, 4.26; Br, 16.07; Found: C, 60.22; H, 4.54; Br, 16.20.

PREPARATION 5

Preparation of compound 29:

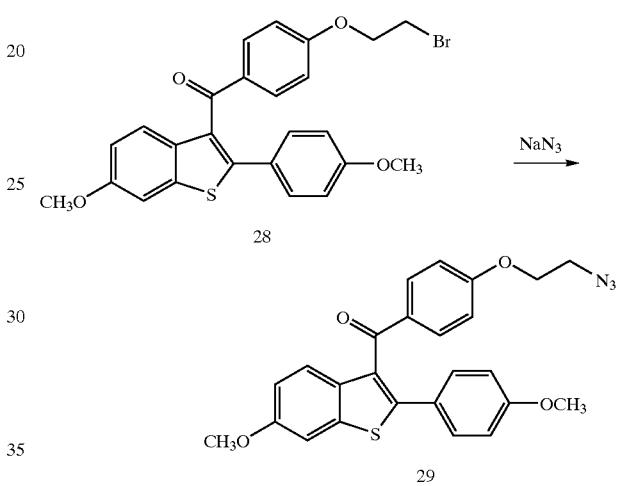

Compound 28 (0.5 g, 1.0 mmol) and sodium azide (0.12 g, 2.0 mmol) were stirred in DMF for 144 hours followed by warming to 80° C. for 1 hr. The solvent was removed under reduced pressure and the residue chromatographed on silica gel using ethyl acetate/hexanes (1:1), affording 0.41 g (89%) of compound 29.

$^1$H-NMR (DMSO-d$_6$) δ 7.64–7.66 (m, 3H), 7.28–7.33 (m, 3H), 6.85–6.99 (m, 5H), 4.15–4.18 (m, 2H), 3.82 (s, 3H), 3.65 (s, 3H), 3.60–3.63 (m, 2H); FD$^+$-MS for C$_{25}$H$_{21}$N$_3$O$_4$S=459; Elemental Analysis C$_{25}$H$_{21}$N$_3$O$_4$S -Calculated: C, 65.35; H, 4.61; N, 9.14; Found: C, 65.55; H, 4.79; N, 9.17.

PREPARATION 6

Preparation of compound 30:

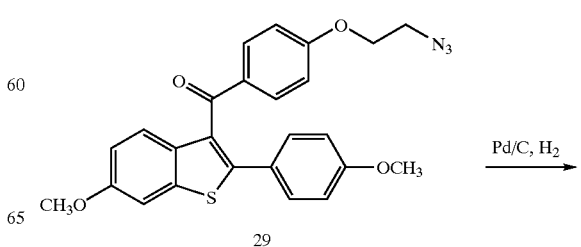

-continued

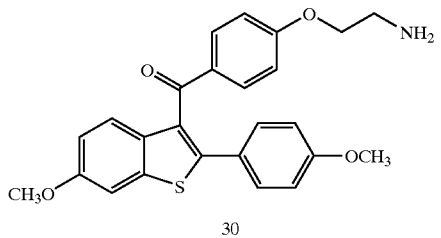

Compound 29 (11.1 g, 24.2 mmol) in 50 ml of THF and 85 ml ethanol, with 1.5 g 5% Palladium on carbon was hydrogenated at room temperature for 24 hrs. The reaction mixture was filtered, concentrated and recrystallized from ethyl acetate/hexane to afford 6.06 g (58%) of compound 30. The HCl salt of an aliquot was prepared for physical chemistry characterization.

IR (KBr) $v_{max}$ 3418, 2937, 2836, 1634, 1598, 1574, 1531, 1498, 1473, 1438, 1350, 1294, 1251, 1167, 1112, 1046,1025, 830; $^1$H-NMR (DMSO-d$_6$) δ 8.22–8.23 (br s, 2H), 7.64–7.61 (t, 3H), 7.28–7.31 (d, 3H), 4.19–4.20 (m, 2H), 3.82 (s, 3H), 3.69 (s, 3H), 3.15–3.17 (m, 2H); FD$^+$-MS for $C_{25}H_{24}ClNO_4S$=433; Elemental Analysis $C_{25}H_{24}ClNO_4S$ -Calculated: C, 63.89; H, 5.15; N, 2.98; Found: C, 63.80; H, 5.11; N, 2.83.

EXAMPLE 5

Preparation of compound 17:

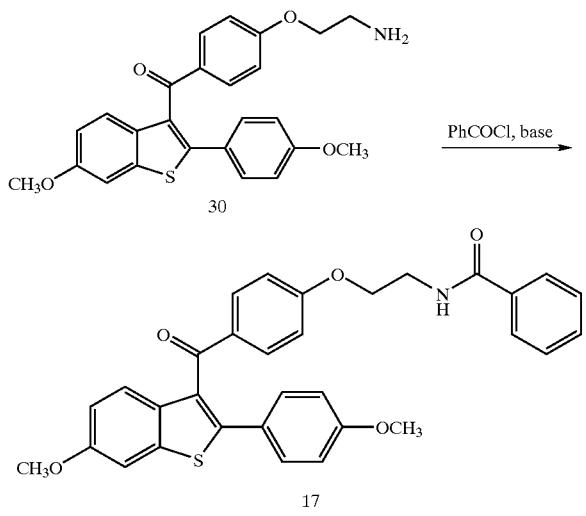

Compound 30 (1.0 g, 2.3 mmol), benzoyl chloride (0.35 g, 2.5 mmol) and sodium hydroxide (0.1 g, 2.5 mmol) was stirred in 75 ml water at room temperature for 18 hrs. The product was extracted with ethyl acetate, dried over sodium sulfate, concentrated and chromatographed on silica gel using an ethyl acetate/methanol gradient yielding 1.03 g (83%) of compound 17.

$^1$H-NMR (DMSO-d$_6$) δ 8.63 (m, 1H), 7.80–7.82 (m, 1H), 7.63–7.68 (m, 3H), 7.40–7.49 (m, 3H), 7.26–7.31 (m, 4H), 6.85–6.98 (m, 5H), 4.19–4.20 (m, 2H), 3.15–3.17 (m, 2H); FD$^+$-MS for $C_{32}H_{27}NO_5S$=537; Elemental Analysis $C_{32}H_{27}NO_5S$ -Calculated: C, 71.49; H, 5.06; N, 2.60; Found: C, 71.72; H, 5.12; N, 2.62.

The following compounds for which physical data are shown may be prepared in a manner analogous with procedures detailed in the above examples.

EXAMPLE 6

Compound 3:

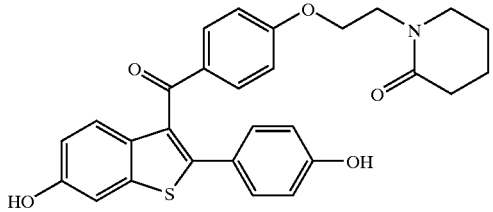

$^1$H NMR (DMSO-d$_6$) δ 9.78(s, 1H), 9.72(s, 1H), 7.66 (d, 2H, J=10 Hz), 7.34 (s, 1H), 7.26 (d, 1H, J=10 Hz), 7.18 (d, 2H, J=10 Hz), 6.91 (d, 2H, J=10 Hz), 6.84 (dd, 1H, J=10 Hz), 6.66 (d, 2H, J=10 Hz), 4.12 (t, 2H, J=8 Hz), 3.58(t, 2H, J=8 Hz), 2.16 (bs, 2H), 1.64 (bs, 4H); EI MS for $C_{28}H_{25}NO_5S$=487 (M*); Elemental Analysis $C_{28}H_{25}NO_5S$ -Calculated: C, 68.98; H, 5.17; N, 2.87; Found: C, 69.08; H, 5.08; N, 2.69.

EXAMPLE 7

Compound 4:

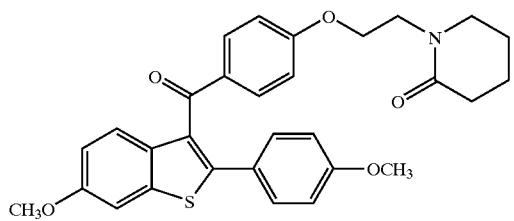

$^1$H NMR (CDCl$_3$) δ 7.77 (d, 2H, J=10 Hz), 7.53 (d, 1H, J=10 Hz), 7.35 (m, 3H), 6.96 (dd, 1H, J=10 Hz, J=3 Hz), 6.75 (dd, 4H, J=10 Hz, J=3 Hz), 4.16 (t, 2H, J=8 Hz), 3.89 (s, 3H), 3.74 (s, 3H), 3.68(t, 2H, J=8 Hz), 3.45 (bs, 2H), 2.34 (bs, 2H), 1.88 (bs, 4H); FD MS for $C_{30}H_{29}NO_5S$=515 (M*); Elemental Analysis $C_{30}H_{29}NO_5S$ -Calculated: C, 69.88; H, 5.67; N, 2.72; Found: C, 69.71; H, 5.67; N, 2.73.

EXAMPLE 8

Compound 5:

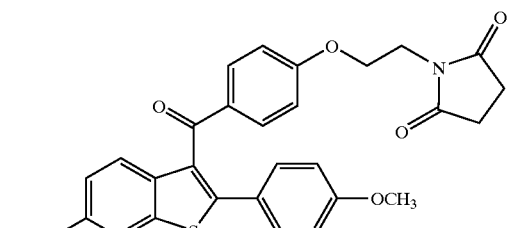

$^1$H NMR (CDCl$_3$) δ 7.74 (d, 2H, J=9.7 Hz), 7.53 (d, 1H, J=9. 7 Hz), 7.33 (m, 3H), 6.97 (dd, 1H, J=9.7 Hz), 6.77 (d, 2H, J=9.7 Hz), 6.73 (d, 2H, J=9.7 Hz), 4.12 (t, 2H, J=9.7 Hz), 3.9 (m, 5H), 2.75(s, 3H), 2.67 (s, 4H); FD+ MS=515.

EXAMPLE 9

Compound 6:

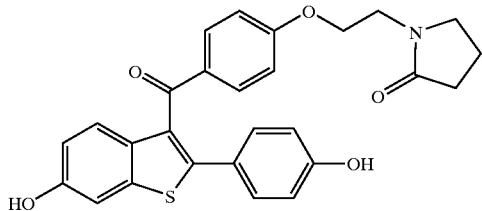

IR (KBr) $v_{max}$ 3228, 2973, 1659, 1597, 1537, 1499, 1467, 1420, 1359, 1258, 1165, 1116, 1037, 908, 835, 807, 540; $^1$H-NMR (DMSO $d_6$) δ 9.75 (s, 1H), 9.71 (s, 1H), 7.56–7.62 (m, 3H), 7.21–7.32 (m, 2H), 6.84–6.91 (d, 2H, J=6.3 Hz), 6.66–6.84 (d, 2H), 4.07–4.09 (t, 2H, J=5.3 Hz), 3.47–3.48 (t, 2H, J=5.3 Hz), 2.47–2.48 (t, 2H), 2.12–2.18 (m, 2H), 1.84–1.87 (m, 2H); FD+ MS for $C_{27}H_{23}NO_5S$=473; Elemental Analysis $C_{27}H_{23}NO_5S$ -Calculated: C, 68.48; H, 4.90; N, 2.96; Found: C, 68.21; H, 5.13; N, 2.99.

EXAMPLE 10

Compound 8:

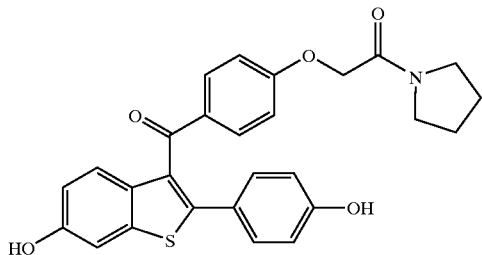

$^1$H-NMR (acetone-$d_6$) δ 8.68 (bs, 2H), 7.71 (d, J=8.7 Hz, 2H), 7.33–7.40 (m, 2H), 7.26 (d, J=8.9 Hz, 2H), 6.82–6.94 (m, 3H), 6.73 (d, J=8.8 Hz, 2H), 4.53 (s, 2H), 3.51 (t, J=4.0 Hz, 2H), 3.36 (t, J=4.1 Hz, 2H), 1.71–1.90 (series of m, 4H), IR (CHCl$_3$) 3307 (b), 1645 cm$^{-1}$; FD$^+$-MS 473 (M$^+$).

EXAMPLE 11

Compound 9:

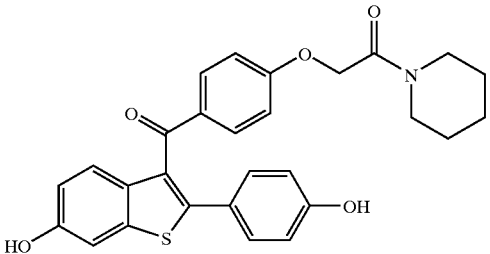

$^1$H-NMR (acetone-$d_6$) δ 8.68 (bs, 1H), 8.60 (bs, 1H), 7.70 (d, J=8.9 Hz, 2H), 7.35–7.41 (m, 2H), 7.27 (d, J=8.9 Hz, 2H), 6.84–6.95 (m, 3H), 6.73 (d, J=8.7 Hz, 2H), 4.81 (s, 2H), 3.47 (t, J=4.1 Hz, 4H), 1.43–1.67 (series of m, 6H), IR (CHCl$_3$) 3300 (b), 1639 cm$^{-1}$; FD$^+$-MS 487 (M$^+$); Elemental Analysis $C_{28}H_{25}NO_5S$ -Calculated: C, 68.98; H, 5.17; N, 2.87; Found: C, 67.50; H, 5.43; N, 2.84.

EXAMPLE 12

Compound 10:

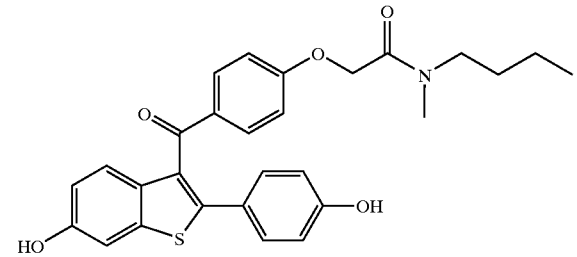

$^1$H-NMR (DMSO-$d_6$) δ 9.81 (s, 1H), 9.73 (s, 1H), 7.64 (d, J=9.0 Hz, 2H), 7.33 (d, J=2.3 Hz, 1H), 7.15–7.25 (m, 3H), 6.82–6.91 (m, 3H), 6.69 (d, J=8.8 Hz, 2H), 4.85 (s, 2H), 3.20–3.35 (m, 5H), .1.5–1.57 (series of m, 4H), 0.81–0.92 (m, 3H); IR (CHCl$_3$) 3300 (b), 1625 cm$^{-1}$; FD$^+$-MS 489 (M$^+$); Elemental Analysis $C_{28}H27NO_5S$ -Calculated: C, 68.69; H, 5.56; N, 2.86; Found: C, 67.75; H, 5.49; N, 2.88.

EXAMPLE 13

Compound 12:

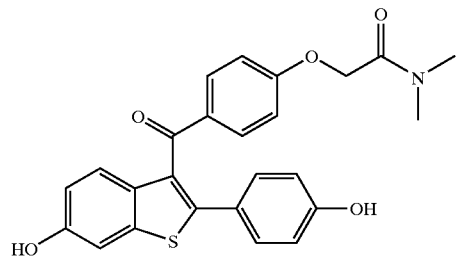

$^1$H-NMR (MeOD $d_4$) δ 7.71 (d, 2H, J=9.0 Hz), 7.4 (d, 1H, J=9.0 Hz), 7.26 (s, 1H), 7.20 (d, 2H, J=9.0 Hz), 6.87 (m, 2H), 6.42 (d, 2H, J=9.0 Hz), 3.05 (s, 3H), 2.96 (s, 3H); FD$^+$-MS=447; Elemental Analysis $C_{25}H_{21}NO_5S$ -Calculated: C, 67.10; H, 4.73; N, 3.13; Found: C, 67.32; H, 4.94; N, 2.99.

EXAMPLE 14

Compound 13:

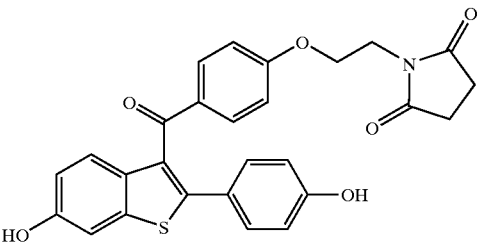

$^1$H NMR (MeOD $d_4$) δ 7.68 (d, 2H, J=9.0 Hz), 7.41 (d, 1H, J=9.0 Hz), 7.26 (s, 1H), 7.18 (d, 2H, J=9.0 Hz), 6.86 (d, 1H, J=9.0 Hz), 6.80 (d, 2H, J=9.0 Hz), 6.63 (d, 2H, J=9.0 Hz), 4.15 (t, 2H, J=6 Hz), 3.84 (t, 2H, J=6 Hz), 2.62 (s, 4H); FD$^+$-MS=487; Elemental Analysis $C_{27}H21NO_6S$ -Calculated: C, 66.52; H, 4.34; N, 2.87; Found: C, 66.65; H, 4.55; N, 2.83.

EXAMPLE 15

Compound 14:

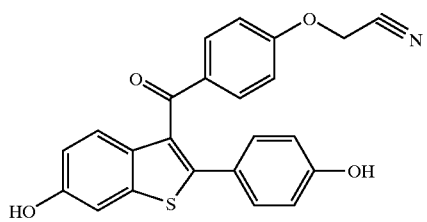

¹H-NMR (acetone-d6) δ 8.63 (bs, 1H) 7.79 (d, J=8.9 Hz, 2H), 7.36–7.46 (m, 2H), 7.28 (d, J=9.1 Hz, 2H), 7.02 (d, J=8.9 Hz, 2H), 6.93 (dd, J=8.9 Hz, 2.8 Hz, 1H), 6.73 (d, J=9.0,2H), 5.12 (s, 2H); FD⁺-MS 401 (M+).

EXAMPLE 16

Compound 15:

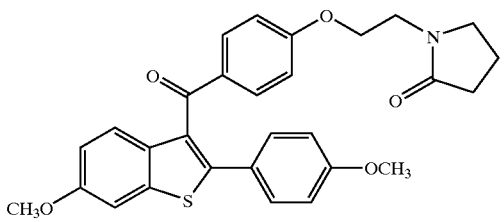

¹H NMR (CDCl₃) δ 7.56–7.82 (t, 2H, J=5.8 Hz), 7.33–7.36 (t, 2H, J=2.9 Hz), 6.97–6.98 (m, 1H), 6.73–6.80 (m, 4H), 4.08–4.14 (m, 2H), 3.89–3.92 (d, 3H, J=8.5 Hz), 3.76–3.78 (d, 3H, J=8.7 Hz), 3.64–3.70 (m, 2H), 3.51–3.58 (m, 2H), 2.38–2.43 (m, 2H), 2.03–2.08 (m, 2H); FD⁺-MS for C₂₉H₂₇NO₅S=501.

EXAMPLE 17

Compound 16:

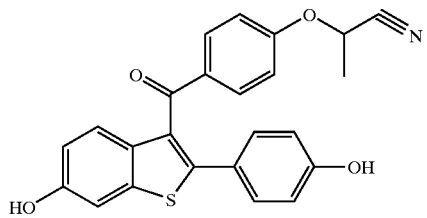

¹H-NMR δ 8.63 (bs, 1H) 7.79 (d, J=8.8 Hz, 2H), 7.38–7.47 (m, 2H), 7.25 (d, J=9.0 Hz, 2H), 7.05 (d, J=8.9 Hz, 2H), 6.93 (dd, J=8.7, 2.8 Hz, 1H), 6.73 (d, J=9.0,2H), 5.38 (q, J=6.1 Hz, 2H), 1.74 (d, J=6.0 Hz, 3H); FD⁺-MS 415 (M+); Elemental Analysis C₂₄H₁₇NO₄S -Calculated: C, 69.38; H, 4.12; N, 3.37; Found: C, 69.19; H, 4.40; N, 3.08.

EXAMPLE 18

Compound 18:

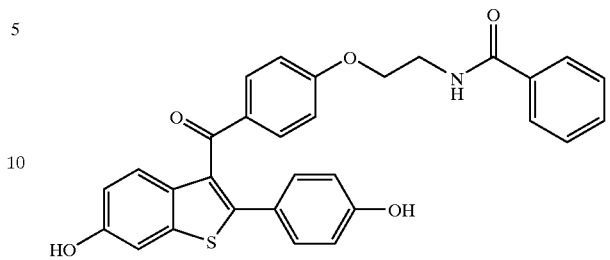

IR (KBr) ν$_{max}$ 3311, 2953, 1637, 1597, 1538, 1502, 1468, 1422, 1358, 1309, 1258, 1166, 1113, 1038, 907, 836; ¹H-NMR (DMSO d₆) δ 9.68–9.73 (d, 2H), 8.63 (m, 1H), 7.76–7.81 (d, 2H, J=8.6 Hz), 7.61–7.64 (d, 2H, J=8.8 Hz), 7.38–7.48 (m, 2H), 7.30 (s, 1H), 7.12–7.20 (m, 4H), 6.91–6.93 (m, 2H, J=7.0 Hz), 6.81–6.82 (m, 1H), 6.62–6.64 (d, 2H, J=6.6 Hz), 4.11–4.13 (m, 2H), 3.56–3.60 (m, 2H); FD⁺-MS for C₃₀H₂₃NO₅S=5409; Elemental Analysis C₃₀H₂₃NO₅S -Calculated: C, 70.71; H, 4.55; N, 2.75; Found: C, 70.67; H, 4.66; N, 2.68.

EXAMPLE 19

Compound 19:

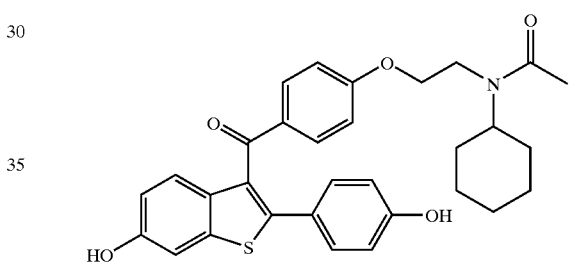

IR (KBr) ν$_{max}$ 3375, 2932, 2856, 1598, 1539, 1506, 1468, 1422, 1354, 1306, 1258, 1166, 1113, 1035, 907, 836, 647, 620; ¹H-NMR (DMSO d₆) δ 9.70 (br s, 2H), 7.61–7.64 (d, 2H, J=8.4 Hz), 7.50 (s, 1H), 7.21–7.24 (d, 1H), 7.13–7.19 (d, 2H), 6.76–6.98 (m, 3H), 6.61–6.63 (d, 2H, J=7.7 Hz), 3.40–3.45 (m, 2H), 2.81–2.84 (m, 2H), 0.85–1.81 (m, 11H); FD⁺-MS for C₃₁H₃₁NO₅S=529; Elemental Analysis C₃₁H₃₁NO₅S -Calculated: C, 70.30; H, 5.90; N, 2.64; Found: C, 70.43; H, 6.10; N, 2.55.

EXAMPLE 20

Compound 20:

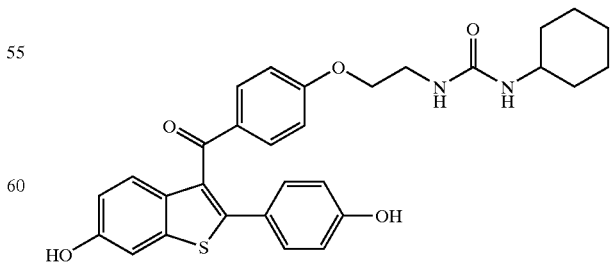

IR (KBr) ν$_{max}$ 3363, 2931, 2854, 1598, 1565, 1503, 1468, 1422, 1357, 1315, 1255, 1166, 1038, 908, 836, 808, 672; ¹H-NMR (DMSO d₆) δ 9.70–9.75 (d, 2H), 7.62–7.65 (d, 2H, J=7.9 Hz), 7.31 (s, 1H), 7.21–7.24 (d, 1H), 7.13–7.16 (d, 2H, J=8.2 Hz), 6.88–6.91 (d, 2H, J=8.3 Hz), 6.81–6.84 (d, 1H), 6.64–6.66 (d, 2H, J=8.3 Hz), 3.96–3.99 (m, 2H), 3.30 (m, 2H), 1.28–1.60 (m, 5H), 0.96–1.27 (m, 6H); FD$^+$-MS for $C_{30}H_{30}N_2O_5S$=530; Elemental Analysis $C_{30}H_{30}N_2O_5S$ -Calculated: C, 67.91; H, 5.70; N, 5.28; Found: C, 68.12; H, 5.99; N, 5.39.

EXAMPLE 21

Compound 21:

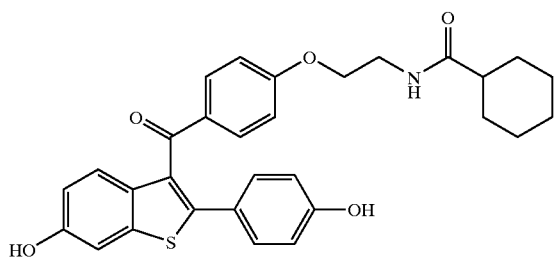

$^1$H-NMR (DMSO d$_6$) δ 9.70 (s, 2H), 7.60–7.65 (d, 2H, J=8.6 Hz), 7.50 (s, 1H), 7.14–7.22 (m, 2H), 6.80–7.00 (m, 4H), 6.62–6.66 (m, 2H), 4.01–4.04 (m, 2H), 3.50–3.70 (m, 2H), 1.40–1.78 (m, 5H), 1.01–1.39 (m, 6H); FD$^+$-MS for $C_{30}H_{29}NO_5S$=519.

EXAMPLE 22

Compound 22:

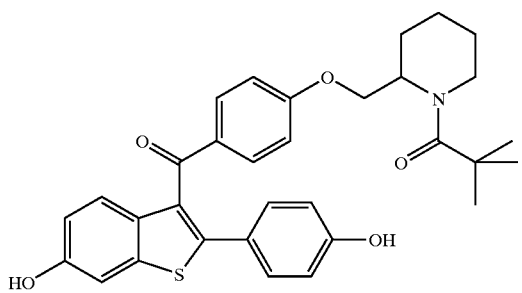

IR (CHCl$_3$) ν$_{max}$ 3298, 3025, 3010, 2946, 1600, 1262, 1166; $^1$H-NMR (MeOD d$_4$) δ 7.68–7.71 (d, 2H, J=8.8 Hz), 7.38–7.41 (d, 1H, J=8.7 Hz) 7.24–7.25 (d, 1H, J=2.5 Hz), 7.16–7.19 (d, 2H, J=8.6 Hz), 6.83–6.87 (m, 3H), 6.60–6.63 (d, 2H, J=8.6 Hz), 4.35–4.20 (m, 11H), 1.25 (s, 9H); $^{13}$C-NMR (MeOD d$_4$) δ 194.39, 178.33, 163.40, 158.07, 155.62, 142.72, 140.28, 133.19, 132.37, 130.62, 130.24, 130.09, 124.89, 123.62, 115.38, 114.93, 114.28, 106.82, 65.17, 50.36, 38.89, 27.70, 25.53, 25.16, 19.09; FD$^+$-MS for $C_{32}H_{33}O_5S$=543; Elemental Analysis $C_{32}H_{33}O_5S$ -Calculated: C, 70.69; H, 6.12; N, 2.58; Found: C, 70.47; H, 6.13; N, 2.34.

EXAMPLE 23

Compound 23:

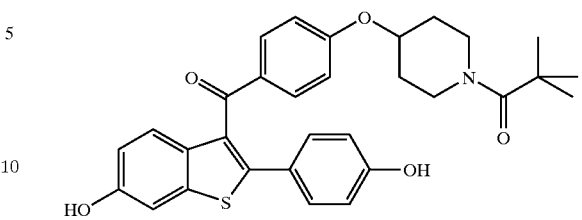

IR (CHCl$_3$) ν$_{max}$ 3293, 3021, 3010, 1598, 1254, 1166; $^1$H-NMR (MeOD d$_4$) δ 7.65–7.68 (d, 2H, J=8.9 Hz), 7.45–7.48 (d, 1H, J=8.8 Hz), 7.25–7.26 (d, 1H, J=2.2 Hz), 7.14–7.17 (d, 2H, J=8.6 Hz), 6.81–6.89 (m, 3H), 6.59–6.62 (d, 2H, J=8.6 Hz), 4.63–4.69 (m, 1H), 3.79–3.89 (m, 2H), 3.51–3.60 (m, 2H), 1.89–1.95 (m, 2H), 1.62–1.71 (m, 2H), 1.27 (s, 9H); $^{13}$C-NMR (MeOD d$_4$) δ 194.06, 177.14, 161.67, 157.87, 155.43, 143.21, 140.04, 132.92, 132.18, 130.38, 130.16, 129.85, 124.71, 123.51, 115.10, 115.06, 114.74, 106.57, 71.80, 41.75, 38.40, 30.41, 27.28; FD$^+$-MS for $C_{31}H_{31}O_5S$=529.

EXAMPLE 24

Compound 24:

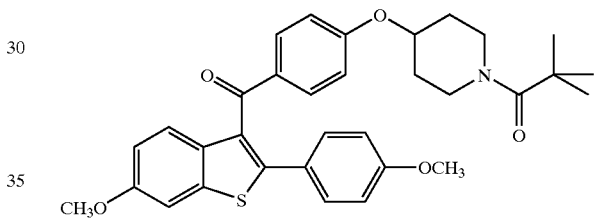

IR (CHCl$_3$) ν$_{max}$ 3008, 1609, 1599, 1476, 1253, 1191, 1188; $^1$H-NMR (CDCl$_3$) δ 7.73–7.76 (d, 2H, J=8.7 Hz), 7.53–7.56 (d, 1H, J=8.9 Hz), 7.31–7.34 (m, 3H), 6.94–6.98 (dd, 1H, J=8.8 Hz, J=2.0 Hz), 6.73–6.76 (m, 4H), 4.52–4.60 (m, 1H), 3.88 (s, 3H), 3.74 (s, 3H), 1.67–3.85 (m, 8H), 1.28 (s, 9H); $^{13}$C-NMR (CDCl$_3$) δ 193.03, 176.31, 161.29, 159.73, 157.66, 142.78, 140.03, 133.91, 132.40, 130.58, 130.49, 130.31, 126.03, 124.06, 115.14, 114.81, 113.99, 104.46, 71.86, 55.60, 55.23, 41.64, 38.67, 30.61, 28.34, 25.57; FD$^+$-MS for $C_{33}H_{35}O_5S$=557.

EXAMPLE 25

Compound 26:

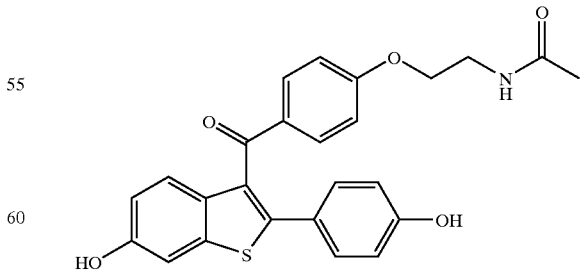

$^1$H-NMR (DMSO d$_6$) δ 9.75 (d, 2H), 7.62–7.65 (d, 2H), 7.31 (d, 1H), 7.16–7.19 (d, 2H), 6.83–6.91 (m, 4H), 6.66–6.68 (m, 2H), 3.97–3.99 (m, 2H), 3.59–3.81 (m, 2H), 1.77 (s, 3H); FD$^+$-MS for $C_{25}H_{21}NO_5S$=447.

The compounds of formula I, II, or III of the present invention are useful for alleviating the symptoms of post-menopausal sundrome, particularly osteoporosis, assocated cardiovascular diseases, particularly hyperlipidemia, and estrogen-dependent cancer, particularly estrogen-dependent breast and uterine carcinoma. The term "alleviating" is defined to include prophylactically treating a person at risk of incurring one or more symptoms or pathological conditions of post-menopauysal syndrome, holding in check such symptoms or pathological conditions, and treating existing symptoms or pathological conditions, as appropriate.

Compounds of the present invention are also effective for inhibiting uterine fibroid disease and endometriosis in women, and smooth muscle cell proliferation in humans. The following non-limiting biological test examples illustrate the methods of the present invention.

Biological Test Procedures

I. General Preparation for Post-Menopausal Rat Model

In the examples illustrating the methods, a post-menopausal model was used in which effects of different treatments upon various biological parameters were determined, including serum cholesterol concentration, uterine weight, eosinophil peroxidase activity, MCF-7 cell proliferation, and bone density.

Seventy-five day old female Sprague Dawley rats (weight range of 200 to 225 g) were obtained from Charles River Laboratories (Portage, Mich.). The animals were either bilaterally ovariectomized (OVX) or exposed to a sham surgical procedure (Intact) at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

II. Four Day Dosing Regimen

After a one week acclimation period (therefore, two weeks post-OVX), daily dosing with test compound was initiated. 17α-Ethynyl estradiol ($EE_2$) (Sigma Chemical Co., St. Louis, Mo.), an orally available form of estrogen, or the test compound were given orally, unless otherwise stated, as a suspension in 1% carboxymethyl cellulose or dissolved in 20% cyclodextrin. Animals were dosed daily for 4 days. Following the dosing regimen, animals were weighed and anesthetized with a ketamine:xylazine (2:1, v:v)mixture. A blood sample was collected by cardiac puncture. The animals were then sacrificed by asphyxiation with $CO_2$, the uterus was removed through a midline incision, and a wet uterine weight was determined.

A. Cholesterol Analysis

Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotometrically at 500 nm. Cholesterol concentration was then calculated against a standard curve. The entire assay was automated using a Biomek Automated Workstation.

B. Uterine Eosinophil Peroxidase (EPO) Assay

Uteri were kept at 4° C. until time of enzymatic analysis. The uteri were then homogenized in 50 volumes of 50 mM Tris buffer (pH-8.0) containing 0.005% Triton x-100. Upon addition of 0.01% hydrogen peroxide and 10 mM o-phenylenediamine (final concentrations) in Tris buffer, increase in absorbance was monitored for one minute at 450 nm. The presence of eosinophils in the uterus, as measured by assay of eosinophil peroxidase activity, is an indication of estrogenic activity of a compound. The maximal velocity of a 15 second interval was determined over the initial, linear portion of the reaction curve.

C. Results

Data presented in Table 1 below show comparative results among control ovariectomized rats, rats treated with $EE_2$, and rats treated with certain compounds of the present invention. Although $EE_2$ caused a decrease in serum cholesterol when orally administered at 0.1 mg/Kg/day, it also exerted a marked stimulatory action on the uterus so that the uterine weight of $EE_2$ treated rats was substantially greater than the uterine weight of ovariectomized test animals. This uterine response to estrogen is well recognized in the art.

In contrast, the compounds of the present invention substantially reduce serum cholesterol compared to the ovariectomized control animals without the general increase of uterine weight that is associated with estrogen compounds known in the art. This benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the present invention did not cause an increase in the number of eosinophils observed in the stromal layer of ovariectomized rats, or in rare instances an increase only at the highest concentrations tested, as measured by assay of eosinophil peroxidase activity, while $EE_2$ caused a substantial, expected increase in eosinophil infiltration.

The data presented in Table 1 reflect the response of 5 to 6 rats per treatment.

TABLE 1

| Compound | Dose (mg/kg) | Uterine Weight (% inc. OVX) | Uterine EPO (Vmax) | Serum Cholesterol (% dec. OVX) |
|---|---|---|---|---|
| ethynyl estradiol | 0.1 | 235.2* | 120.0* | 89.6* |
| 3 | 0.1 | 13.3 | 8.0 | 38.1* |
|  | 1 | 17.8 | 7.8 | 45.8* |
|  | 10 | 57.6* | 8.9 | 72.4* |
| 6 | 0.1 | −9 | 3.6 | 33.6* |
|  | 1 | 15.4 | 1.4 | 52.4* |
|  | 10 | 40.3* | 3.7 | 67.5* |
| 7 | 0.1 | −0.5 | 5.2 | 3.4 |
|  | 1 | −16.2 | 3.7 | 14.6 |
|  | 10 | 8.4 | 4.7 | −41.9* |
| 8 | 0.1 | −4.7 | 3.6 | 17.4 |
|  | 1 | 25.6* | 6.1 | 69.6* |
|  | 10 | 61.7* | 39.1 | 70.3* |
| 8 | 0.01 | −22.9 | 3.5 | 27.2 |
|  | 0.1 | −12.6 | 4.4 | 25.8 |
|  | 1 | −11.5 | 3.7 | 39.4* |
|  | 10 | −1.3 | 3.7 | 64.5* |
| 9 | 0.1 | −10.0 | 2.8 | 4.2 |
|  | 1 | 6.5 | 3.6 | 22.0 |
|  | 10 | 51.7* | 32 | 74.3* |
| 10 | 0.1 | 1.5 | 4.3 | −40.0* |
|  | 1 | −6.7 | 3.1 | 19.1 |
|  | 10 | 38.0* | 17.0 | 67.1* |
| 12 | 0.1 | −7.7 | 3.7 | 27.8* |
|  | 1 | 15.4 | 6.7 | 48.2* |
|  | 10 | 60.7* | 122.3* | 71.2* |
| 13 | 0.1 | 22.2 | 1.9 | 37.6* |
|  | 1 | 7.2 | 1.7 | 12.6 |
|  | 10 | −4.0 | 2.5 | 30.1* |
| 14 | 0.1 | 18.8 | 3.3 | 3.3 |
|  | 1 | 14.6 | 2.4 | 23.7 |
|  | 10 | 124.6* | 145.8* | 91.1 |
| 16 | 0.1 | 0.7 | 2.3 | 3.4 |
|  | 1 | 27.4 | 3.9 | 28.8* |

TABLE 1-continued

| Compound | Dose (mg/kg) | Uterine Weight (% inc. OVX) | Uterine EPO (Vmax) | Serum Cholesterol (% dec. OVX) |
|---|---|---|---|---|
|  | 10 | 99.2* | 23.4 | 71.2* |
| 18 | 0.1 | 16.1 | 3.2 | −10.8 |
|  | 1 | 25.7 | 3.6 | −12.2 |
|  | 10 | 12.6 | 3.6 | 12.8 |
| 19 | 0.1 | 7 | 5.4 | 14.5 |
|  | 1 | −25.5* | 3.7 | 20.1 |
|  | 10 | 47.0* | 29.3* | 52.2* |
| 20 | 0.1 | −29.9 | 3.0 | −27.2 |
|  | 1 | −27.4 | 2.5 | −6.0 |
|  | 10 | −32.7 | 2.9 | −15.4 |
| 21 | 0.1 | −5.5 | 3.1 | 9.3 |
|  | 1 | −11.5 | 2.6 | 0.5 |
|  | 10 | 8.6 | 2.4 | 24.0* |
| 22 | 0.1 | 1.9 | 3.5 | 22.1* |
|  | 1 | 19.6 | 20.0 | 36.2* |
|  | 10 | 46.9* | 69.5* | 71.5* |
| 23 | 0.1 | −4.3 | 1.6 | −17.4 |
|  | 1 | 0.8 | 3.8 | −5.2 |
|  | 10 | 22.3 | 6.7 | 55.8* |
| 26 | 0.1 | −17.5 | 1.3 | 15.8 |
|  | 1 | −28.8* | 0.7 | 19.0 |
|  | 10 | 25.8* | 13.6 | 32.8 |

*indicates value is significantly different than OVX control.

In addition to the demonstrated benefits of the compounds of the present invention, especially when compared to estradiol, the above data clearly demonstrate that these compounds are not estrogen mimetics. Furthermore, no deleterious toxicological effects (survival) were observed with treatment by any of the compounds of the present invention.

III. Thirty-Five Day Dosing Regimen

Following the General Preparation procedure described above, the rats were treated daily for 35 days (6 rats per treatment group) and sacrificed by decapitation on the 36th day. The 35 day time period was sufficient to allow maximal effect on bone density, measured as described herein. At the time of sacrifice, the uteri were removed, dissected free of extraneous tissue, and the fluid contents were expelled before determination of wet weight in order to confirm estrogen deficiency associated with complete ovariectomy. Uterine weight was routinely reduced about 75% in response to ovariectomy. The uteri were then placed in 10% neutral buffered formalin to allow for subsequent histological analysis.

A. Bone Density Assay

The right tibias were excised and scanned at the distal metaphysis 1 mm from the patellar groove with single photon absorptiometry. Results of the densitometer measurements represent a calculation of bone density as a function of the bone mineral content and bone width.

In accordance with the procedures outlined above, compounds of the present invention and $EE_2$ in 20% hydroxypropyl β-cyclodextrin were orally administered to test animals.

B. Results

Ovariectomy of the test animals caused a significant reduction in tibia density compared to intact, vehicle treated controls. Orally administered $EE_2$ prevented this loss, but the risk of uterine stimulation with this treatment is ever-present.

The compounds of the present invention also prevented bone loss in a general, dose-dependent manner. Accordingly, the compounds of the present invention are useful for the treatment of post-menopausal syndrome, particularly osteoporosis.

IV. MCF-7 Proliferation Assay

MCF-7 breast adenocarcinoma cells (ATCC HTB 22) were maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 μg/ml) (maintenance medium). Ten days prior to assay, MCF-7 cells were switched to maintenance medium supplemented with 10% dextrancoated charcoal stripped fetal bovine serum (DCC-FBS) assay medium) in place of 10% FBS to deplete internal stores of steroids. MCF-7 cells were removed from maintenance flasks using cell dissociation medium (Ca++/Mg++ free HBSS (phenol red-free) supplemented with 10 mM HEPES and 2 mM EDTA). Cells were washed twice with assay medium and adjusted to 80,000 cells/ml. Approximately 100 ml (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 ml transferred to triplicate microcultures followed by 50 ml assay medium for a final volume of 200 ml. After an additional 48 hours at 37° C. in a 5% $CO_2$ humidified incubator, microcultures were pulsed with tritiated thymidine (1 uCi/well) for 4 hours. Cultures were terminated by freezing at −70° C. for 24 hours followed by thawing and harvesting of microcultures. Samples were counted by liquid scintillation. Results in Table 3 below show the $ED_{50}$ for certain compounds of the present invention.

TABLE 3

| Compound | $ED_{50}$ (nM) |
|---|---|
| 3 | 600 |
| 7 | >1000 |
| 8 | 10 |
| 9 | 10 |
| 10 | 50 |
| 13 | >1000 |
| 14 | 0.05 |
| 16 | 0.02 |
| 18 | 500 |
| 19 | 0.1 |
| 20 | 0.1 |
| 22 | 0.01 |
| 23 | 4.0 |

V. DMBA-Induced Mammary Tumor Inhibition

Estrogen-dependant mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to unifor mly distribute the various sizes of tumors in the treated and control groups such that average-sized tumors are equivalently distributed between test groups. Control groups and test groups for each experiment contain 5 to 9 animals.

Compounds of the current invention are administered either through intraperitoneal injections in 2% acacia, or orally. orally administered compounds are either dissolved or suspended in 0.2 ml corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

VI. Uterine Fibrosis Test Procedures

Test 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Test 2

The same procedure is used as in Test 1, except the period of administration is 6 months.

Test 3

The same procedure is used as in Test 1, except the period of administration is 1 year.

Test 4

A. Induction of Fibroid Tumors in Guinea Pig

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Uterine Fibroid Tissue Implantation in Nude Mice

Tissue from human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric lavage on a daily basis for 3–16 weeks and implants are removed and measured for growth or regression. At the time of sacrifice, the uteri is harvested to assess the status of the organ.

Test 5

Tissue from human uterine fibroid tumors is harvested and maintained, in vitro, as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

VII. Endometriosis Test Procedure

In Tests 1 and 2, effects of 14-day and 21-day administration of compounds of the present invention on the growth of explanted endometrial tissue can be examined.

Test 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals remaining uterus, and ovaries, where applicable, are removed and prepared for histological examination. The ovaries and adrenals are weighed.

Test 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 receive intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Test 3

A. Surgical Induction of Endometriosis

Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

B. Endometrial Tissue Implantation in Nude Mice

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric lavage on a daily basis for 3–16 weeks, and implants are removed and measured for growth or regression. At the time of sacrifice, the uteri is harvested to assess the status of the intact endometrium.

Test 4

Tissue from human endometrial lesions is harvested and maintained in vitro as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Activity in any of the above assays indicates that the compounds of the present invention are useful in the treatment of endometriosis.

VIII. Inhibition of Aortal Smooth Cell Proliferation/ Restenosis Test Procedure

Compounds of the present invention have capacity to inhibit aortal smooth cell proliferation. This can be demonstrated by using cultured smooth cells derived from rabbit aorta, proliferation being determined by the measurement of DNA synthesis. Cells are obtained by explant method as described in Ross, *J. of Cell Bio.* 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 mg/ml streptomycin, 1 mC/ml $^3$H-thymidine, 20 ng/ml platelet-derived growth factor, and varying concentrations of the present compounds. Stock solution of the compounds is prepared in dimethyl sulphoxide and then diluted to appropriate concentration (0.01–30 mM) in the above assay medium. Cells are then incubated at 37° C. for 24 hours under 5% $CO_2$/95% air. At the end of 24 hours, the cells are fixed in methanol. $^3$H thymidine incorporation in DNA is then determined by scintillation counting as described in Bonin, et al., *Exp. Cell Res.* 181: 475–482 (1989).

Inhibition of aortal smooth muscle cell proliferation by the compounds of the present invention are further demonstrated by determining their effects on exponentially growing cells. Smooth muscle cells from rabbit aortae are seeded in 12 well tissue culture plates in DMEM containing 10% fetal bovine serum, 2 MM L-glutamine, 100 U/ml penicillin, and 100 µg/ml streptomycin. After 24 hours, the cells are attached and the medium is replaced with DMEM containing 10% serum, 2 mM L-glutamine, 100 U/ml penicillin, 100 µg/ml streptomycin, and desired concentrations of the compounds. Cells are allowed to grow for four days. Cells are treated with trypsin and the number of cells in each culture is determined by counting using a ZM-Coulter counter.

Activity in the above tests indicates that the compounds of the present invention are of potential in the treatment of restenosis.

Combination Therapy

The present invention also provides a method of alleviating post-menopausal syndrome in women which comprises the aforementioned method using compounds of the present invention and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, supra, indicates that the combination treatments are useful for alleviating the symptoms of post-menopausal symptoms in women. various forms of estrogen and progestin are commercially available. Estrogen-based agents include, for example, ethenyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of the present invention are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The compounds of this invention can be administered by a variety of routes including oral, rectal, transdermal, subucutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of the current invention, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients, and salt must be compatible with the other ingredients of the formulation, and not deleterious to the recipient thereof.

Pharmaceutical formulations of the present invention can be prepared by procedures known in the art using well known and readily available ingredients. For example, the compounds of the current invention, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of the present invention, alone or in combination with a pharmaceutical agent of the present invention, generally will be administered in a convenient formulation.

The following formulation examples only are illustrative and are not intended to limit the scope of the present invention.

Formulations

In the formulations which follow, "active ingredient" means a compound of formula I, II, or III.

Formulation 1: Gelatin Capsules
Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3: Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool. An intravenous formulation is prepared as follows:

Formulation 7: Intravenous Solution

| Ingredient | Quantity |
| --- | --- |
| Active ingredient | 50 mg |
| Isotonic saline | 1,000 ml |

| Ingredient | Quantity (mg/capsule) |
|---|---|
| Formulation 8: Combination Capsule I | |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |
| Formulation 9: Combination Capsule II | |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |
| Formulation 10: Combination Tablet | |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

The solution of the above ingredients is intravenously administered to a patient at a rate of about 1 ml per minute.

We claim:

1. A compound of formula I

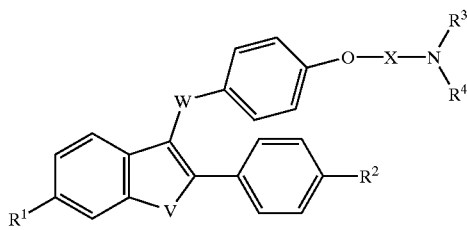

wherein $R^1$ is OH, O—C(O)—($C_1$-$C_6$ alkyl), O—C(O)—O($C_1$-$C_6$ alkyl), O—C(O)—Ar, or O—C(O)—O—Ar;

$R^2$ is H, OH, O($C_1$-$C_6$ alkyl), O—C(O)—($C_1$-$C_6$ alkyl), O—C(O)—O($C_1$-$C_6$ alkyl), O—C(O)—Ar, O—C(O)—O—Ar, O—$SO_2$—($C_4$-$C_6$ alkyl), chloro, fluoro, or bromo;

V is S, O, or $CH_2CH_2$;

W is CHOH, C(O), or $CH_2$;

X is $(CH_2)_n$;

$R^3$ and $R^4$ each, independently, are H, $C_1$-$C_6$ alkyl, C(O)—($C_1$-$C_6$ alkyl), C(O)—NH—($C_1$-$C_6$ alkyl), C(O)—Ar, or together with the nitrogen to which they are attached form a 5- or 6-membered imide or cyclic amide;

n is 1, 2, or 3; and

Ar is optionally substituted phenyl;

provided that at least one of $R^3$ and $R^4$ contain a carbonyl functional group.

2. The compound of claim 1 wherein V is S.

3. The compound of claim 1 wherein W is C(O).

4. The compound of claim 1 wherein X is $(CH_2)_2$.

5. The compound of claim 1 wherein $R^3$ and $R^4$ together with the nitrogen to which they are attached form a 5- or 6-membered imide or cyclic amide.

6. The compound of claim 1 wherein $R^2$ is OH, O—C(O)—($C_1$-$C_6$ alkyl), O—C(O)—O($C_1$-$C_6$ alkyl), O—C(O)—Ar, or O—C(O)—O—Ar.

7. The compound of claim 6 wherein V is S, W is C(O), and X is $(CH_2)_2$.

8. The compound of claim 7 wherein $R^3$ and $R^4$ together with the nitrogen to which they are attached form a 5- or 6-membered imide or cyclic amide.

9. A pharmaceutical composition comprising an effective amount of a compound according to claim 1 in combination with a pharmaceutically acceptable carrier, diluent, or excipient.

10. A pharmaceutical composition comprising an effective amount of a compound according to claim 6 in combination with a pharmaceutically acceptable carrier, diluent, or excipient.

11. A pharmaceutical composition comprising an effective amount of a compound according to claim 7 in combination with a pharmaceutically acceptable carrier, diluent, or excipient.

12. A pharmaceutical composition comprising an effective amount of a compound according to claim 8 in combination with a pharmaceutically acceptable carrier, diluent, or excipient.

13. A method for alleviating osteoporosis comprising administering to a woman in need thereof an effective amount of a compound of claim 1.

14. A method for alleviating hyperlipidemia comprising administering to a woman in need of thereof an effective amount of a compound of claim 1.

15. A method for alleviating estrogen-dependent cancer comprising administering to a woman in need thereof an effective amount of a compound of claim 1.

16. A method according to claim 15 wherein the estrogen-dependent cancer is breast or uterine cancer.

17. A method for inhibiting uterine fibroid disease comprising administering to a woman in need thereof an effective amount of a compound of claim 1.

18. A method for inhibiting endometriosis comprising administering to a woman in need thereof an effective amount of a compound of claim 1.

19. A method for inhibiting aortal smooth muscle cell proliferation comprising administering to a person in need thereof an effective amount of a compound of claim 1.

20. A method for inhibiting restenosis comprising administering to a person in need thereof an effective amount of a compound of claim 1.

* * * * *